(12) United States Patent
Abe et al.

(10) Patent No.: US 10,905,473 B2
(45) Date of Patent: Feb. 2, 2021

(54) TRANSVERSE, AND SURGICAL INSTRUMENT

(71) Applicants: ASRO medical, Tsuchiura (JP); UNIVERSITY OF TSUKUBA, Tsukuba (JP)

(72) Inventors: Tetsuya Abe, Ibaraki (JP); Masataka Sakane, Ibaraki (JP); Taira Takato, Tokyo (JP)

(73) Assignees: ASRO medical, Tsuchiura (JP); UNIVERSITY OF TSUKUBA, Tsukuba (JP)

( * ) Notice: Subject to any disclaimer, the term of this patent is extended or adjusted under 35 U.S.C. 154(b) by 0 days.

(21) Appl. No.: 16/077,956

(22) PCT Filed: Jun. 23, 2016

(86) PCT No.: PCT/JP2016/068643
§ 371 (c)(1),
(2) Date: Aug. 14, 2018

(87) PCT Pub. No.: WO2017/141459
PCT Pub. Date: Aug. 24, 2017

(65) Prior Publication Data
US 2019/0125416 A1    May 2, 2019

(30) Foreign Application Priority Data
Feb. 15, 2016  (JP) ................. 2016-025789

(51) Int. Cl.
*A61B 17/70*  (2006.01)
*A61B 17/16*  (2006.01)
*A61B 90/00*  (2016.01)

(52) U.S. Cl.
CPC ...... *A61B 17/7083* (2013.01); *A61B 17/1671* (2013.01); *A61B 17/70* (2013.01);
(Continued)

(58) Field of Classification Search
CPC ............ A61B 17/7049; A61B 17/7077; A61B 17/7067; A61B 17/7089
See application file for complete search history.

(56) References Cited

U.S. PATENT DOCUMENTS 5,281,223 A *  1/1994  Ray ...................... A61B 17/025
                                              606/86 A
5,380,325 A    1/1995  Lahille et al.
(Continued)

FOREIGN PATENT DOCUMENTS

AU        720999 B2    6/2000
EP       2305154 A1    4/2011
(Continued)

OTHER PUBLICATIONS

English Translation of International Preliminary Report on Patentability (Chapter II of the Patent Cooperation Treaty), dated Jul. 4, 2017; IPEA/JP.
(Continued)

*Primary Examiner* — Ellen C Hammond
*Assistant Examiner* — Tara Rose E Carter

(57) ABSTRACT

Problem to be Solved
A traverse that is percutaneously provided and a surgical instrument for percutaneously providing the transverse are provided.
Solution
A rod 10 is placed in each of two rod openings 113, 123 and a transverse bar 130 is inserted in two bar holes 111, 121. Set screws 140, 150 are screwed in screw holes 114, 124. The set screws 140, 150 press the transverse bar 130, thereby restraining the transverse bar 130 in the longitudinal direction. Since portions of the bar holes 111, 121 adjoin the rod openings 113, 123, the pressed transverse bar 130 contacts the rods 10 and pushes the rods 10 against the rod openings 113, 123. A protrusion 127 engages with the rods 10 to
(Continued)

restrain hooks 110, 120 in the longitudinal direction and circumferential direction of the rods 10.

13 Claims, 16 Drawing Sheets

(52) U.S. Cl.
CPC ...... *A61B 17/7034* (2013.01); *A61B 17/7049* (2013.01); *A61B 17/7067* (2013.01); *A61B 17/7077* (2013.01); *A61B 17/7088* (2013.01); *A61B 17/7089* (2013.01); *A61B 2090/061* (2016.02)

(56) References Cited

U.S. PATENT DOCUMENTS

| | | | |
|---|---|---|---|
| 5,814,046 A | 9/1998 | Hopf | |
| 2002/0161368 A1 | 10/2002 | Foley et al. | |
| 2002/0169448 A1* | 11/2002 | Vanacker | A61B 17/7049 606/250 |
| 2004/0116928 A1 | 6/2004 | Young et al. | |
| 2005/0080414 A1 | 4/2005 | Keyer et al. | |
| 2007/0270808 A1 | 11/2007 | Drewry et al. | |
| 2007/0270822 A1* | 11/2007 | Heinz | A61B 17/7062 606/279 |
| 2007/0276367 A1 | 11/2007 | Puno | |
| 2008/0208249 A1* | 8/2008 | Blain | A61B 17/1608 606/207 |
| 2009/0187217 A1* | 7/2009 | Weiman | A61B 17/7052 606/257 |
| 2011/0040301 A1* | 2/2011 | Blain | A61B 17/1608 606/80 |
| 2011/0077690 A1 | 3/2011 | Shin et al. | |
| 2012/0323279 A1 | 12/2012 | Tsuang et al. | |
| 2013/0030469 A1* | 1/2013 | Karas | A61B 17/844 606/264 |
| 2015/0374414 A1 | 12/2015 | Dant et al. | |
| 2016/0038195 A1* | 2/2016 | Genovese | A61B 17/7082 606/79 |
| 2016/0242827 A1* | 8/2016 | Viljoen | A61B 17/7076 |

FOREIGN PATENT DOCUMENTS

| | | |
|---|---|---|
| JP | H06-165789 A | 6/1994 |
| JP | H08-505785 A | 6/1996 |
| JP | H09-510628 A | 10/1997 |
| JP | H10-80432 A | 3/1998 |
| JP | 2003-511190 A | 3/2003 |
| JP | 2006-503672 A | 2/2006 |
| JP | 2007-508118 A | 4/2007 |
| JP | 2009-533173 A | 9/2009 |
| JP | 2009-537242 A | 10/2009 |
| JP | 2013-535306 A | 9/2013 |
| WO | WO-2014/045870 A1 | 3/2014 |
| WO | WO-2015/066325 A1 | 5/2015 |

OTHER PUBLICATIONS

International Search Report issued in PCT/JP2016/068643 (in English and Japanese), dated Aug. 30, 2018; ISA/JP.

Extended European Search Report dated Sep. 23, 2019 in corresponding EP Patent Application No. 16890597.4.

* cited by examiner

TRANSVERSE, AND SURGICAL INSTRUMENT

CROSS REFERENCE TO RELATED APPLICATIONS

This application is a U.S. National Phase Application under 35 U.S.C. 371 of International Application No. PCT/JP2016/068643 filed on Jun. 23, 2016 and published in Japanese as WO 2017/141459 A1 on Aug. 24, 2017. This application is based on and claims the benefit of priority from Japanese Patent Application No. 2016-025789 filed Feb. 15, 2016. The entire disclosures of all of the above applications are incorporated herein by reference.

TECHNICAL FIELD

The present invention relates to a transverse that couples rods that interconnect pedicle screws attached to a spine and to a surgical instrument for attaching the transverse to the rods.

BACKGROUND ART

Posterior fixation surgery in which pedicle screws are screwed into multiple vertebrae making up a spine, rods are attached to the heads of the pedicle screws and the rods are coupled together using a transverse to maintain the positional relationship between the multiple vertebrae has heretofore been known. The pedicle screws are screwed into the left and right pedicles of each vertebra and the left and right columns of the pedicle screws are fixed to the left and right rods, respectively. The left and right rods are coupled using the transverse. In this way, the upper and lower vertebral bodies are coupled together and the vertebrae are settled. The transverse includes accepters and a crosslink. The accepters are attached to the left and right rods. The crosslink includes a shaft and a drilling end and passes through and is fixed to the two accepters (Patent literature 1).

Further, a configuration in which a transverse is attached to the heads of pedicle screws (Patent Literature 2), a configuration in which a transverse is fixed to rods with screws (Patent Literature 3), a configuration in which a transverse whose length and angle are adjustable is fixed to rods (Patent Literature 4), and a configuration in which a transverse is attached to the heads of a plurality of pedicle screws (Patent Literature 5) are also known.

CITATION LIST

Patent Literature

Patent literature 1: US Patent Application Publication No. 2013/0030469
Patent literature 2: National Publication of International Patent Application No. 2009-533173
Patent literature 3: National Publication of International Patent Application No. 2009-537242
Patent literature 4: National Publication of International Patent Application No. 2006-503672
Patent literature 5: National Publication of International Patent Application No. 2009-533173

SUMMARY OF INVENTION

Technical Problem

However, a transverse that is percutaneously provided, a method for percutaneously attaching an accepter to a rod, and a method for percutaneously attaching a crosslink to an accepter are not known. A transverse is therefore attached by making an incision. Incision surgery places considerable burden on patients and therefore is not preferable.

The present invention has been made in light of these problems and an object of the present invention is to provide a transverse that is percutaneously provided and a surgical instrument for percutaneously providing the transverse.

Solution to Problem

A transverse according to a first aspect of the present invention includes a hook that engages with a rod that couples screws inserted in a vertebra, and a transverse bar having a predetermined curvature and provided between a plurality of hooks.

The transverse bar is preferably provided in such a way that the transverse bar passes through a spinous process of the vertebra and preferably includes a bar-holder-receiving recess engageable with a bar holder that holds the transverse bar.

Each of the hooks preferably includes a bar hole through which the transverse bar passes or a rod opening that engages with the rod. Further, each hook preferably includes a bar hole through which the transverse bar passes and a rod opening that engages with the rod and the bar hole preferably communicates with the rod opening. Moreover, each hook preferably includes a hook-holder-receiving recess engageable with a hook holder that holds the hook. Further, preferably, each hook includes a screw hole that communicates with the bar hole and the transverse further includes a set screw that is screwed into the screw hole and, when the set screw enters the screw hole, a tip of the set screw engages with and presses the transverse bar and the transverse bar pressed by the tip of the set screw presses the rod and pushes the rod against the rod opening.

The rod preferably connects a plurality of screws inserted in different vertebrae and the hooks are attached to two rods, one to each rod.

A sizer according to a second aspect of the present invention includes two sizer bars, a centering shaft rotatably supporting the two sizer bars on a predetermine axis, and a lock preventing rotation of the sizer bars with respect to the centering shaft, wherein a rod gripping end that engages with a rod that couples screws inserted in a vertebra is provided at one end of each of the sizer bars.

A scale part that displays a spacing between the rod gripping ends is preferably provided at the other end of the sizer bar and the centering shaft preferably extends from the two sizer bars along a predetermined axis by a predetermined length.

A vertebra awl according to a third aspect of the present invention includes two vertebra awl bars, and a centering shaft rotatably supporting the two vertebra awl bars on a predetermined axis, wherein the centering shaft includes a hole that is coaxial with the predetermined axis, and a sharp-pointed vertebra awl tip configured to make a hole in the vertebra is provided at one end of each of the vertebra awl bars.

A soft-tissue awl according to a fourth aspect of the present invention includes an awl extended rod rotatably supported at one end by a predetermined axis and radially extending from the predetermined axis, and a penetrator having a predetermined curvature and extending from the other end of the awl extended rod, wherein a soft-tissue insertion sharp-pointed tip configured to make a hole in soft tissue is provided at a tip of the penetrator.

A hook holder according to a fifth aspect of the present invention includes a hook holder extended rod rotationally supported at one end by a predetermined axis and radially extending from the predetermined axis, and a hook holder arm extending from the other end of the hook holder extended rod, wherein a hook gripping part configured to grip a hook is provided at a tip of the hook holder arm.

The hook gripping part is openable and closable and the hook holder preferably further includes a hook operating part for opening and closing the hook gripping part.

A bar holder according to a sixth aspect of the present invention includes a bar holder extended rod rotatably supported at one end by a predetermined axis and radially extending from the predetermined axis, and a bar holder arm having a predetermined curvature and extending from another end of the bar holder extended rod, wherein a bar gripping part configured to grip a bar is provided at a tip of the bar holder arm.

The bar gripping part is openable and closable and the bar holder preferably further includes a bar operating part for opening and closing the bar gripping part.

A surgical instrument according to a seventh aspect of the present invention is a surgical instrument used for attaching a transverse and includes the sizer, the vertebra awl, the hook holder, and the bar holder.

The surgical instrument may further include the soft-tissue awl.

Advantageous Effect of Invention

According to the present invention, a transverse that is percutaneously provided and a surgical instrument for percutaneously providing the transverse are provided.

REFERENCE SIGNS LIST

Figure 1:
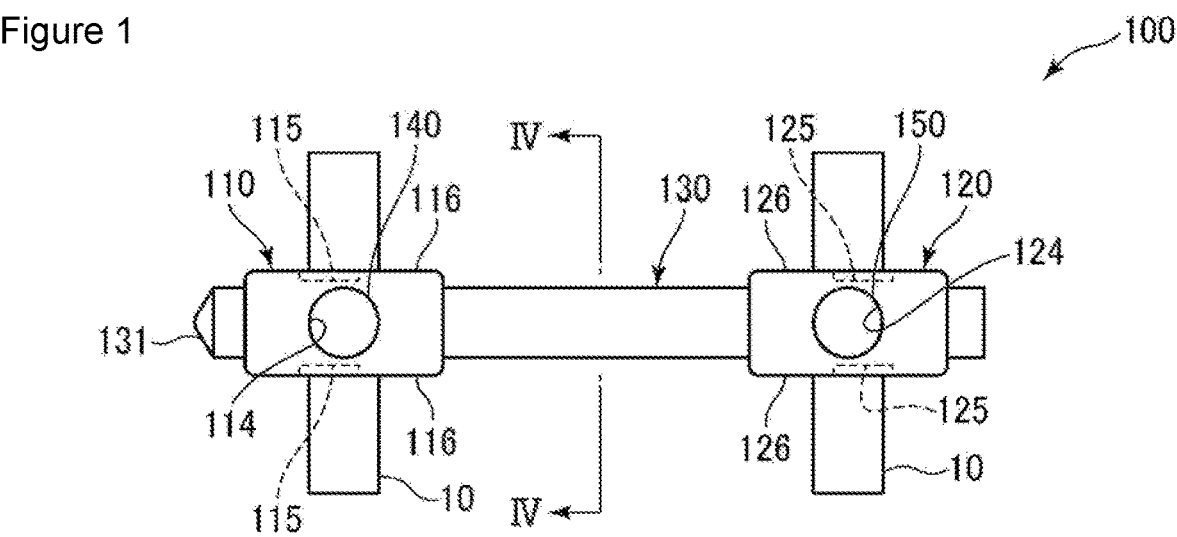
FIG. 1 is a plan view schematically illustrating a transverse.
Figure 2:
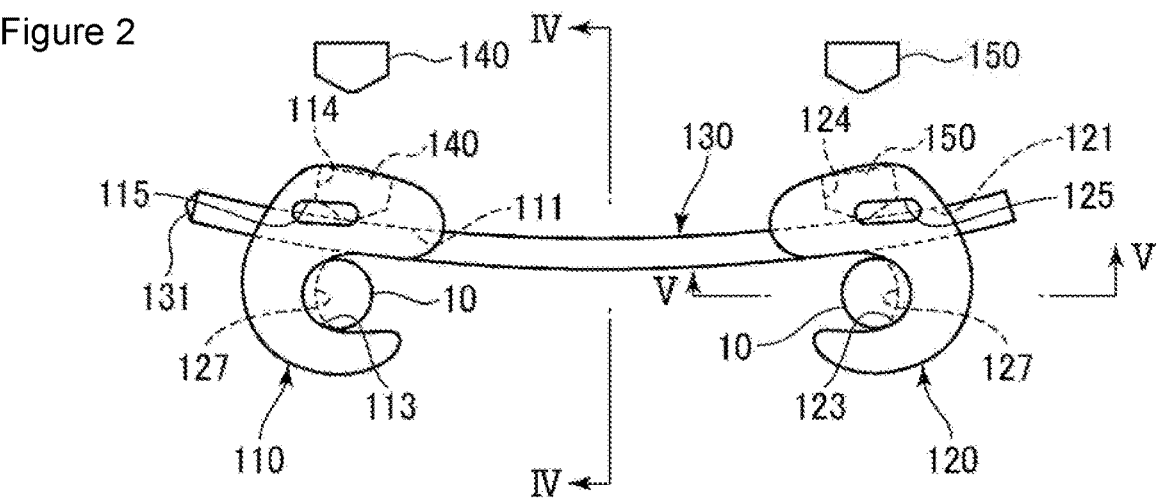
FIG. 2 is a front view schematically illustrating the transverse.

10 Rod
20 Pedicle screw
30 Vertebra
31 Spinous process
100 Transverse
110 Hook
120 Hook
130 Transverse bar
140 Set screw
150 Set screw
200 Sizer
300 Vertebra awl
400 Soft-tissue awl
500 Hook holder
600 Bar holder
700 Set-screw-driver

DESCRIPTION OF EMBODIMENTS

A transverse 100 according to one embodiment of the present invention will be described first with reference to FIGS. 1 to 5.

The transverse 100 mainly includes two hooks 110, 120, a transverse bar 130, and set screws 140, 150.

Each of the hooks 110, 120 has a U-shaped cross section and mainly includes bar hole 111, 121, rod opening 113, 123, screw hole 114, 124 and hook-holder-receiving recess 115, 125.

An inner peripheral surface of the U-shape of each hook 110, 120 forms each rod opening 113, 123. Each of the rod openings 113, 123 is sized so that a rod 10, which will be described later, can easily enter the rod opening 113, 123 and the diameter of the rod opening 113, 123 is such that the rod 10 can be easily received. The rod opening 123 includes a protrusion 127 (see FIG. 5) that runs in the circumferential direction and the rod opening 113 also includes a similar protrusion, which is not depicted. Each of the bar holes 111, 121 is a hole having a rectangular cross section that adjoins a portion of the rod opening 113, 123, that is, opens in the rod opening 113, 123, and passes through the hook 110, 120. The size of the rectangular cross section of the bar holes 111, 121 is slightly larger than a cross section of the transverse bar 130. The screw holes 114, 124 are holes each of which has an axis that intersects the bar hole 111, 121 and has a female-threaded inner peripheral surface. In the front view illustrated in FIG. 2, the bar holes 111, 121 pass through the hooks 110, 120 in the horizontal direction and the screw holes pass from the top surfaces of the hooks 110, 120 toward the bar holes 111, 121.

The hook-holder-receiving recesses 115, 125 are recesses having an oval cross section and one is provided in each of two side surfaces 116, 126 of each hook 110, 120.

The transverse bar 130 has an arch-shaped cross section and curves with a predetermined curvature with respect to the longitudinal direction. One end 131 of the transverse bar 130 has the shape of a bullet. The predetermined curvature is 120 mm, for example. Six varieties of the transverse bar 130 are made available, for example, and the lengths of the varieties are 30 mm, 40 mm, 50 mm, 60 mm, 70 mm and 80 mm, for example.

The set screws 140, 150 are so-called socket set screws (setscrews) which have a pointed tip and a hexagonal or star-shaped groove that is engageable with the tip of a set-screw-driver 700 (see FIG. 11), which will be described later, is provided at their heads.

The hooks 110, 120, the transverse bar 130 and the set screws 140, 150 joined to the rods 10 will be described next.

One rod 10 is placed in each of the two rod openings 113, 114 and the transverse bar 130 is inserted in the two bar holes 111, 121. The set screws 140, 150 are screwed into the screw holes 114, 124. The set screws 140, 150 press the transverse bar 130, thereby restraining the transverse bar 130 in the longitudinal direction. Since a portion of each bar hole 111, 121 adjoins the rod opening 113, 123, the pressed transverse bar 130 contacts the rod 10 and pushes the rod 10 against the opening 113, 123. The protrusion 127 engages with the rod 10 and the hook 110, 120 is restrained in the longitudinal direction and the circumferential direction of the rod 10. The spacing between the two rods 10 is fixed and kept constant by the transverse bar 130 being restrained in the longitudinal direction. In addition, the rotation of the hooks 110, 120 in the circumferential direction of the rods 10 is prevented by the transverse bar 130 being restrained by the two hooks 110, 120. The transverse bar 130 is restrained in the longitudinal direction of the rods 10 by the hooks 110, 120 being restrained in the longitudinal direction of the rods 10.

Figure 3:
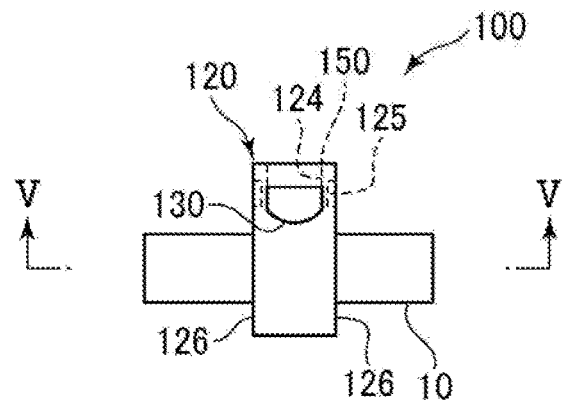
FIG. 3 is a side view schematically illustrating the transverse.
Figure 4:
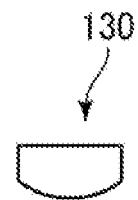
FIG. 4 is a cross-sectional view of the transverse taken along line IV-IV in FIGS. 1 and 2.
Figure 5:
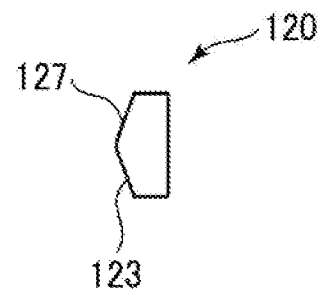
FIG. 5 is a cross-sectional view of a hook taken along line V-V in FIGS. 2 and 3.

Referring to FIG. 3, the length from the top of the rod 10 to the top of the transverse 100 with the transverse 100 attached to the rod 10 is smaller than that of a transverse that is not integral with hooks among conventional transverses. In other words, the transverse 100 according to the present embodiment has a low-profile shape with a shorter length from the top of the rod 10 to the top of the transverse 100 than that of a conventional transverse. A transverse is typically provided under the skin and soft tissue. The transverse provided in this way can push up the skin and the soft tissue toward outside the body and can harm them. Since the transverse 100 according to the present embodiment has a low-profile shape, the transverse 100 does not significantly push up the skin and soft tissue toward outside the body and therefore is unlikely to harm the skin and soft tissue.

A surgical instrument used for attaching the transverse 100 to the rods 10 will be described next. The surgical instrument mainly includes a sizer 200, a vertebra awl 300, a hook holder 500 and a bar holder 600 and optionally includes a soft-tissue awl 400 or a set-screw-driver 700. These instruments will be described below in detail.

Figure 6:
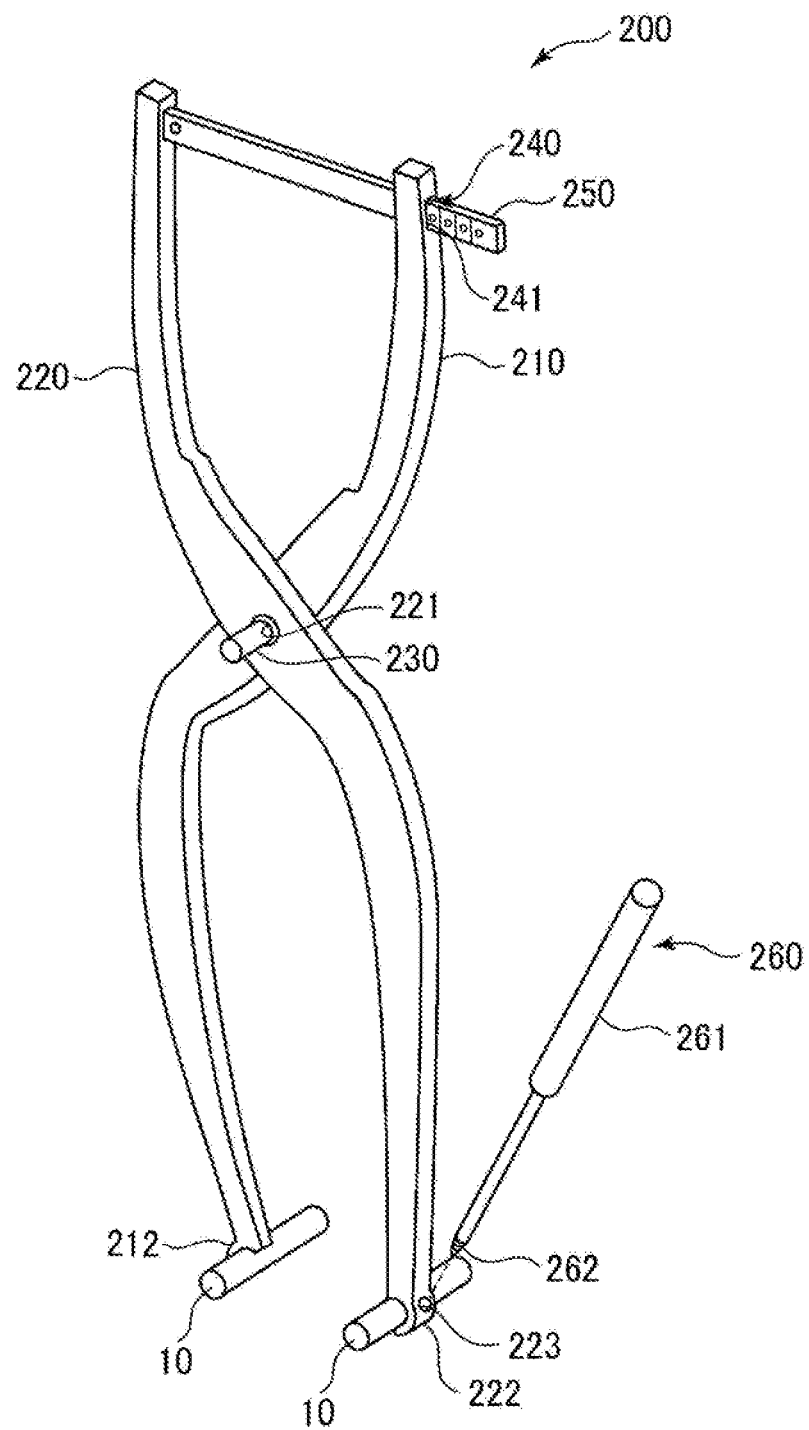
FIG. 6 is a perspective view schematically illustrating a sizer.

The sizer 200 will be described with reference to FIG. 6. The sizer 200 mainly includes two sizer bars 210, 220, a centering shaft 230, a lock 240, and a scale part 250.

The sizer bars 210, 220 are S-shaped thin plates having a thickness of 2.5 mm, for example, and have a hole at or near the inflection point of the S-shape. The diameter of the hole provided in the sizer bar 210 is approximately equal to the diameter of the centering shaft 230 and the centering shaft 230 has a male-threaded cylindrical shape with a diameter of 5 mm, for example, fits into the hole provided in the sizer bar 210 and is fixed to the sizer bar 210. The diameter of the hole 221 provided in the sizer bar 220 is slightly greater than the diameter of the centering shaft 230 and the centering shaft 230 is restrained in the axial direction with respect to the hole 221 and is rotatably supported. The centering shaft 230 has a length in the axial direction greater than the thicknesses of the sizer bars 210 and 220 and has a predetermined length, for example 15 mm.

The lock 240 and the scale part 250 are attached to one end of each of the sizer bars 210, 220. The scale part 250 is a plate-like rectangular solid having a side surface with tick marks. One end of the scale part 250 is fixed to one end of the sizer bar 220 in such a way that the scale part 250 is rotatable around an axis parallel to the axis of the centering shaft 230. The other end of the scale part 250 passes through a hole 241 provided in one end of the sizer bar 210. The lock 240 includes the hole 241. A material having a high friction coefficient is provided in an inner circumferential portion of the hole 241. The material has a friction coefficient that prevents the scale part 250 inserted in the hole 241 from easily moving in the hole 241. This prevents the sizer bars 210 and 220 from easily rotating with respect to the centering shaft 230 and can readily maintain the positional relationship between the sizer bar 210 and the sizer bar 220.

A rod gripping end 212, 222 is provided at the other end of each sizer bar 210, 220. The rod gripping end 212, 222 has a shape where a little over one half of a cylinder is removed at a plane parallel to the central axis of the cylinder. The diameter of the inner circumference of the rod gripping end 212, 222 is slightly greater than the outer diameter of the rod 10. The lock 240 works to prevent the spacing between the rod gripping ends 212, 222 from easily changing. The value of a tick mark in the scale part 250 indicated at an edge of the hole 241 indicates the spacing between the two rods 10. A screw hole 223 that passes from the outer circumferential surface to the inner circumferential surface of each of the rod gripping ends 212, 222 is provided in the rod gripping ends 212, 222. If the two rods 10 are not parallel to each other, there is a possibility that rod gripping ends 212, 222 may not be capable of reliably holding the rods 10 and accordingly the rod gripping ends 212, 222 can be easily disengaged from the rods 10. When the rods 10 need to be reliably held by preventing this, a fixation screw 260 that has a screw gripping part 261 and a screw tip 262 is used. The screw gripping part 261 is cylindrical and the screw tip 262 has a male screw thread cut in its outer periphery and has a pointed tip. When a surgeon grips and rotates the screw gripping part 261, the screw tip 262 is screwed into the screw hole 223, protrudes from the inner circumferential surface of the rod gripping part 212, 222 and caves in the outer periphery surface of the rod 10. This causes the rod gripping end 212, 222 to reliably hold the rod 10.

Figure 7:
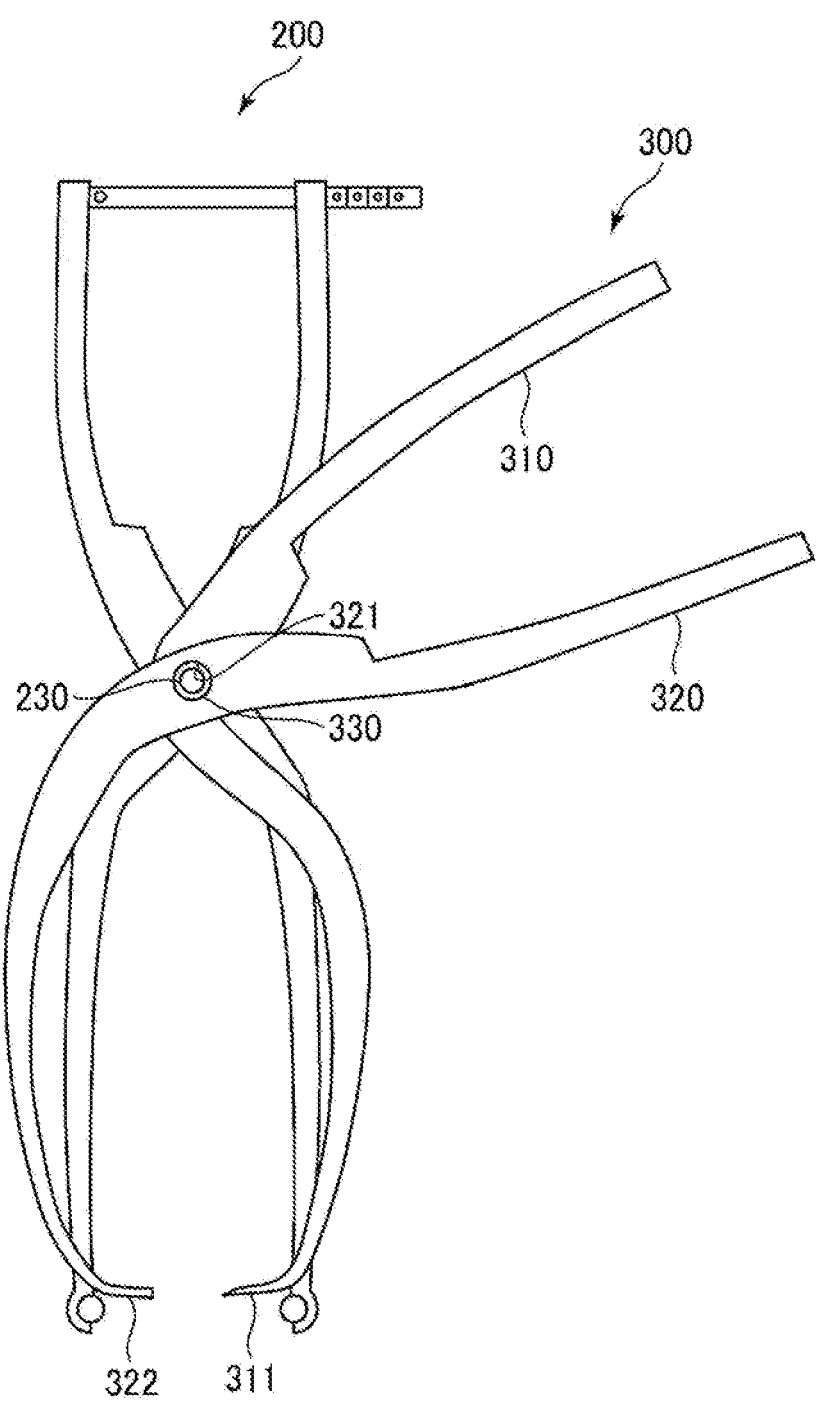
FIG. 7 is a front view schematically illustrating a vertebra awl.

The vertebra awl 300 will be described next with reference to FIG. 7. The vertebra awl 300 mainly includes a first vertebra awl bar 310, a second vertebra awl bar 320, and a hollow shaft 330.

The first vertebra awl bar 310 is an S-shaped thin plate with a thickness of 5 mm, for example, and has a hole, not depicted, at or near the inflection point of the S-shape. The second vertebra awl bar 320 is a sickle-shaped thin plate and has a hole 321 in a central portion. The hole in the first vertebra awl bar 310 and the hole 321 in the second vertebra awl bar 320 have a diameter slightly greater than the outer diameter of the hollow shaft 330. When the first vertebra awl bar 310 and the second vertebra awl bar 320 are attached to the hollow shaft 330, the first vertebra awl bar 310 and the second vertebra awl bar 320 are restrained in the axial direction with respect to the hollow shaft 330 and are rotatably supported.

The length of the centering shaft 230 in the axial direction is greater than the sum of the thicknesses of the sizer bars 210 and 220, the first vertebra awl bar 310 and the second vertebra awl bar 320.

A sharp-pointed vertebra awl tip 311 is provided at one end of the first vertebra awl bar 310 and a vertebra awl recess 322 that has a recess at its tip is provided at one end of the second vertebra awl bar 320. The end of the first vertebra awl bar 310 and the end of the second vertebra awl bar 320 are bent at a right angle to the axis of the hollow shaft 330 in such a way that the ends align with each other when the first vertebra awl bar 310 and the second vertebra awl bar 320 turn around the axis of the hollow shaft 330 and contact with each other.

When the vertebra awl 300 is used, the centering shaft 230 is inserted into the inner periphery of the hollow shaft 330 and a nut, not depicted, is screwed onto the male screw of the centering shaft 230, thereby fixing the vertebra awl 300 in the axial direction. This allows the first vertebra awl bar 310 and the second vertebra awl bar 320 to turn around the axis of the centering shaft 230. The distance from the axis of the centering shaft 230 to the end of the sharp-pointed vertebra awl tip 311 is determined in accordance with the position of a hole to be made in the spinous process of the vertebra.

Figure 8:
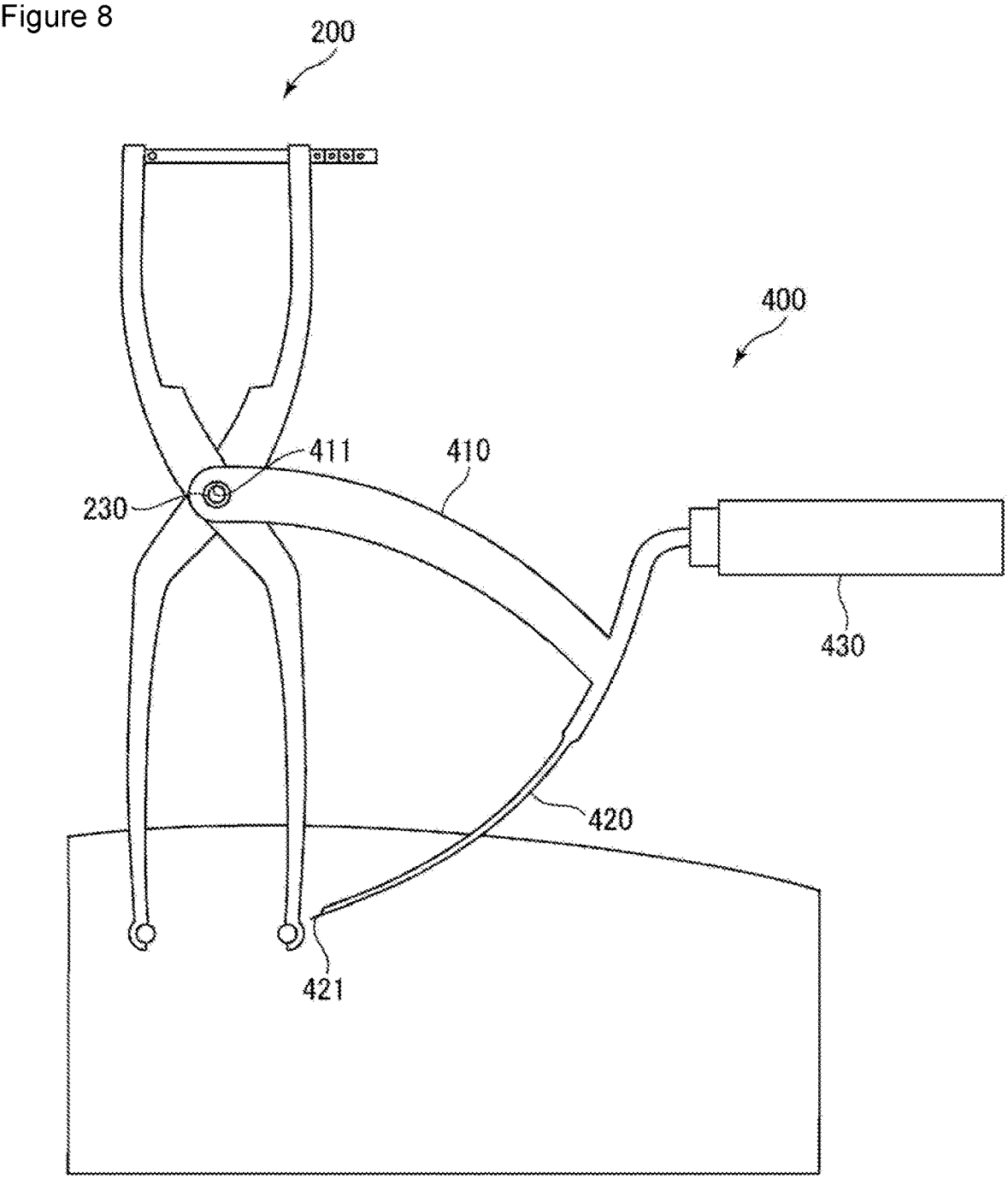
FIG. 8 is a front view schematically illustrating a soft-tissue awl.

The soft-tissue awl 400 will be described next with reference to FIG. 8. The soft-tissue awl 400 mainly includes an awl extended rod 410, a penetrator 420 and an awl handle 430.

The awl extended rod 410 is an arcuate thin plate with a thickness of 5 mm, for example, and has a hole 411 at one end thereof. The centering shaft 230 can loosely fit into the hole 411. The other end of the awl extended rod 410 is connected to the penetrator 420. The penetrator 420 has a needle-like shape curved into an arc with a predetermined curvature. The center of the arc of the penetrator 420 coincides with the center of the hole 411. The curvature of the penetrator 420 is equal to the curvature of the transverse bar 130. The tip of the penetrator 420 is pointed and forms a soft-tissue insertion sharp-pointed tip 421. The awl handle 430 is attached to the posterior end of the penetrator 420.

The length of the centering shaft 230 in the axial direction is greater than the sum of the thicknesses of sizer bars 210 and 220 and the soft-tissue awl 400.

When the soft-tissue awl 400 is used, the centering shaft 230 is inserted into the hole 411 and a nut, not depicted, is screwed on the male screw of the centering shaft 230 to fix the soft-tissue awl 400 in the axial direction. This allows the soft-tissue awl 400 to turn around the axis of the centering shaft 230, that is, allows the penetrator 420 to turn around the axis of the centering shaft 230. The distance from the axis of the centering shaft 230 to the soft-tissue insertion sharp-pointed tip 421 is determined in accordance with a position in which the transverse bar 130 is provided.

Figure 9:
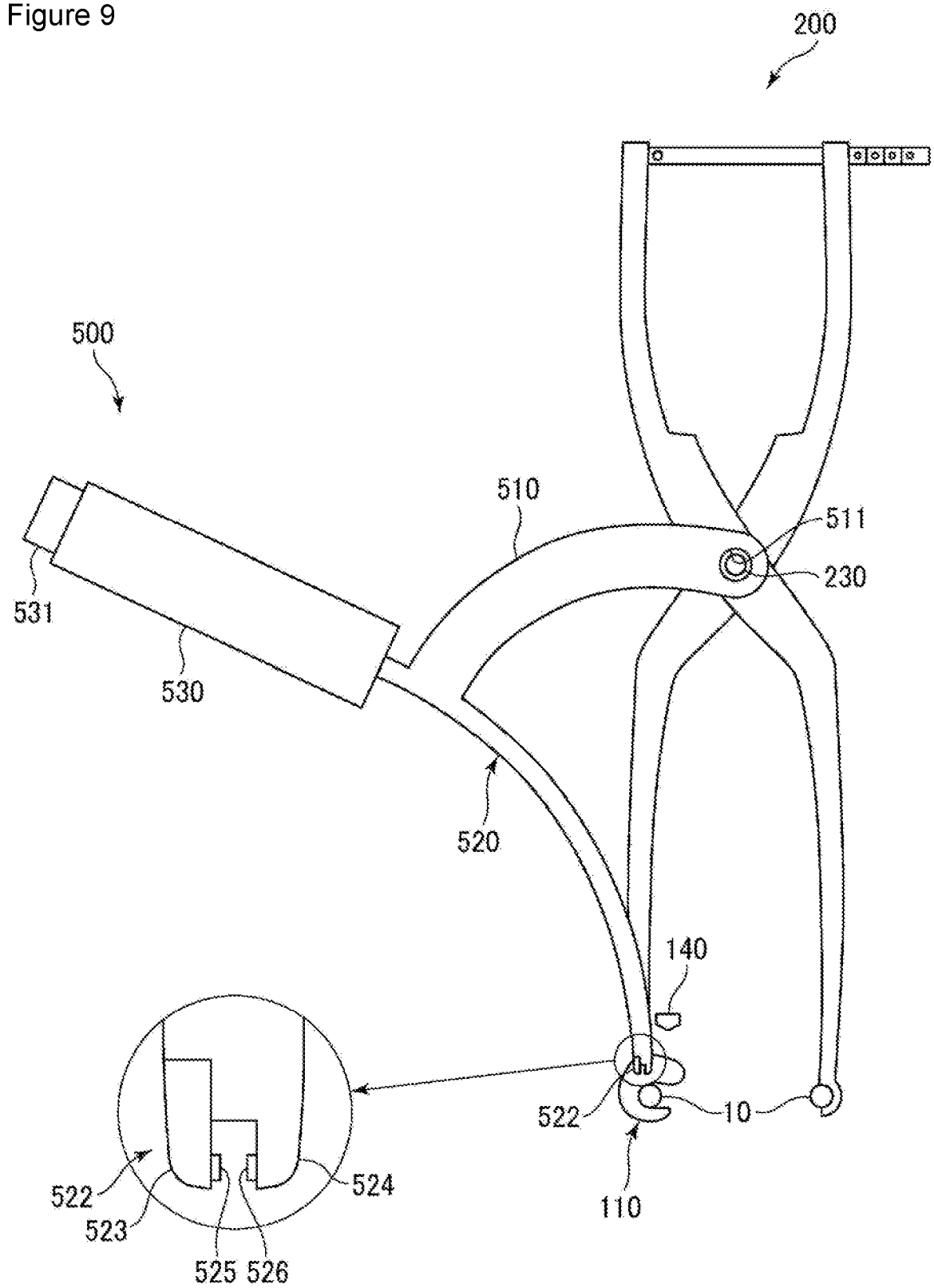
FIG. 9 is a front view schematically illustrating a hook holder.

The hook holder 500 will be described next with reference to FIG. 9. The hook holder 500 mainly includes a hook holder extended rod 510, a hook holder arm 520 and a hook holder handle 530.

The hook holder extended rod 510 is an arcuate thin plate with a thickness of 5 mm, for example, and has a hole 511 at one end thereof. The centering shaft 230 can loosely fit into the hole 511. The other end of the hook holder extended rod 510 is connected to the hook holder arm 520. The hook holder arm 520 is an arcuate thin plate and includes a hook gripping part 522 at its tip. The hook holder handle 530 is attached to the posterior end of the hook holder arm 520. The hook holder handle 530 is provided with a hook operating part 531.

The hook gripping part 522 mainly includes a movable part 523, a fixed part 524, a protrusion 525 and a protrusion 526 that have an oval cross section. The protrusion 525 protrudes from the movable part 523 and the protrusion 526 protrudes from the fixed part in such a way as to face the protrusion 525. The protrusion 525 and the protrusion 526 are slightly smaller in size than the hook-holder-receiving recesses 115, 125. The movable part 523 is movable along the direction in which the protrusion 525 and the protrusion 526 protrude, in such a way as to vary the spacing between the protrusion 525 and the protrusion 526. The movable part 523 is connected to the hook operating part 531 through wire or the like, not depicted, passing inside the hook holder arm 520.

The hook operating part 531 is provided rotatably on the hook holder handle 530. When the hook operating part 531 is rotated clockwise while the movable part 523 is closed, that is, while the spacing between the protrusion 525 and the protrusion 526 is smallest, the wire or the like is reeled and the movable part 523 pulled by the wire or the like moves to widen the spacing between the protrusion 525 and the protrusion 526. On the other hand, when the hook operating part 531 is rotated counterclockwise while the movable part 523 is open, that is, while the spacing between the protrusion 525 and the protrusion 526 is widened, the wire or the like is unreeled and the movable part 523, which has lost the force acting from the wire or the like, moves to narrow the spacing between the protrusion 525 and the protrusion 526. In this way, the hook holder 500 can hold or release the hooks 110, 120.

The length of the centering shaft 230 in the axial direction is greater than the sum of the thicknesses of the seizer bars 210 and 220 and the hook holder 500.

When the hook holder 500 is used, the centering shaft 230 is inserted into the hole 511 and, by screwing a nut, which is not depicted, onto the male screw of the centering shaft 230, the hook holder 500 is fixed in the axial direction. This allows the hook holder 500 to turn around the axis of the centering shaft 230, that is, allows the hook gripping part 522 to turn around the axis of the centering shaft 230.

The distance from the bar hole 111, 121 in the hook attached to the hook gripping part 522 to the axis of the centering shaft 230 is determined in accordance with the distance from the axis of the centering shaft 230 to the rod gripping end 212, 222, that is, the positional relationship between the axis of the centering shaft 230 and the rod 10.

Figure 10:
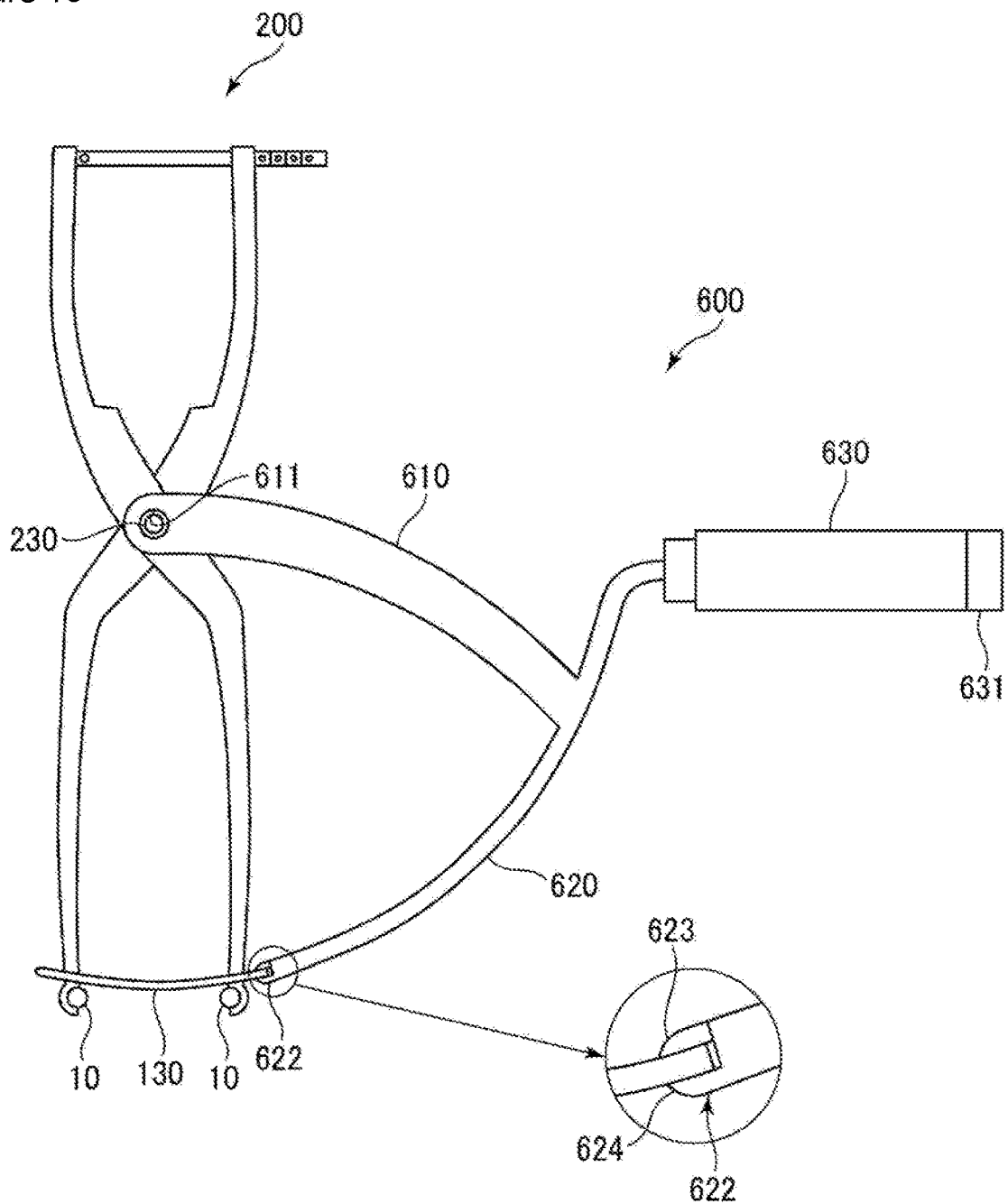
FIG. 10 is a front view schematically illustrating a bar holder.

The bar holder 600 will be described next with reference to FIG. 10. The bar holder 600 mainly includes a bar holder extended rod 610, a bar holder arm 620 and a bar holder handle 630.

The bar holder extended rod 610 is an arcuate thin plate with a thickness of 5 mm, for example, and has a hole 611 at one end thereof. The centering shaft 230 can loosely fit into the hole 611. The other end of the bar holder extended rod 610 is connected to the bar holder arm 620. The bar holder arm 620 is a thin plate curved into an arc with a predetermined curvature and includes a bar gripping part 622 at its tip. The center of the arc of the bar holder arm 620 coincides with the center of the hole 611. The curvature of the bar holder arm 620 is equal to the curvature of the transverse bar 130 and the penetrator 420. The bar holder handle 630 is attached to the posterior end of the bar holder arm 620. The bar holder handle 630 is provided with a bar operating part 631.

The bar gripping part 622 mainly includes a movable part 623 and a fixed part 624. The movable part 623 is movable so as to change the spacing between the movable part 623 and the fixed part 624. The movable part 623 is connected to the bar operating part 631 through wire or the like, not depicted, passing inside the bar holder arm 620.

The bar operating part 631 is provided rotatably on the bar holder handle 630. When the bar operating part 631 is rotated clockwise while the movable part 623 is closed, that is, while the spacing between the movable part 623 and the fixed part 624 is smallest, the wire or the like is reeled and the movable part 623 pulled by the wire or the like moves to widen the spacing between the movable part 623 and the fixed part 624. On the other hand, when the bar operating part 631 is rotated counterclockwise while the movable part 623 is open, that is, while the spacing between the movable part 623 and the fixed part 624 is widened, the wire or the like is unreeled and the movable part 623, which has lost the force acting from the wire or the like, moves to narrow the spacing between the movable part 623 and the fixed part 624. In this way, the bar holder 600 can hold or release the transverse bar 130.

The length of the centering shaft 230 in the axial direction is greater than the sum of the thicknesses of the sizer bars 210 and 220 and the bar holder 600 and is preferably about equal to the sum of the thicknesses of the sizer bars 210 and 220, the hook holder 500, the bar holder 600 and a nut, which will be described later.

When the bar holder 600 is used, the centering shaft 230 is inserted into the hole 611 and, by screwing the nut, which is not depicted, onto the male screw of the centering shaft 230, the bar holder 600 is fixed in the axial direction. This allows the bar holder 600 to turn around the axis of the centering shaft 230, that is, allows the bar gripping part 622 to turn around the axis of the centering shaft 230.

The distance from the bar gripping part 622 to the axis of the centering shaft 230 is determined so as to be equal to the distance from the axis of the centering shaft 230 to the sharp-pointed vertebra awl tip 311 and the vertebra awl recess 322, that is, the distance between the axis of the centering shaft 230 when the sizer 200 is fixed to the rod 10 and a hole 32 (see FIG. 15) made in a spinous process 31, which will be described later.

Figure 11:
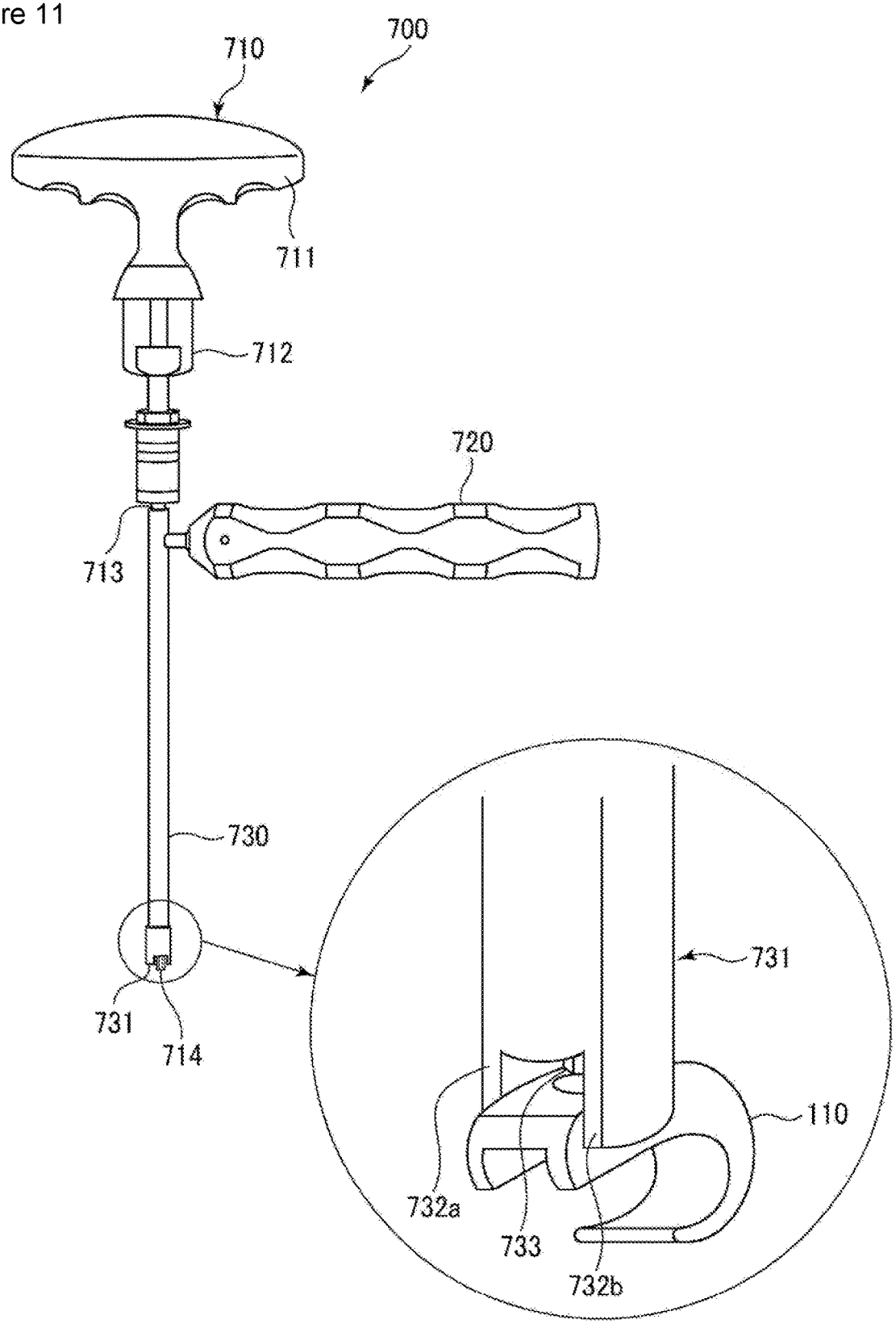
FIG. 11 is a front view schematically illustrating a set-screw-driver.

The set-screw-driver 700 will be described next with reference to FIG. 11. The set-screw-driver 700 mainly includes a gripping rotation part 710, a gripping fixed part 720 and a holding tube 730.

The gripping rotation part 710 includes a T-shaped handle 711, a torque management mechanism 712, and a driver shaft 713. The T-shaped handle 711 has a T-shape that is easy to grip with a human hand. The torque management mechanism 712 extends from the T-shaped handle 711 along the axis of rotation of the T-shaped handle 711. The torque management mechanism 712 controls a rotary torque transferred from the T-shaped handle 711 to the driver shaft so that the rotary torque does not exceed a desired value. The driver shaft 713 is a cylindrical shaft that extends from the torque management mechanism 712 along the axis of rotation of the T-shaped handle 711 and includes a driver part 714 at its tip. The driver part 714 has a hexagonal column shape, a star column shape, or a cylindrical shape that has a hexagonal-columnar or star-columnar internal surface and is engageable with grooves or ridges provided in the heads of the set screws 140 and 150. The gripping fixed part 720 has a substantially cylindrical shape and its outer periphery has a plurality of radially slightly protruding portions. The plurality of portions allows the gripping fixed part 720 to be easily firmly gripped with a human hand. The holding tube 730 has a cylindrical shape having an internal diameter slightly greater than the outer diameter of the driver shaft 713. The tip 731 of the holding tube 730 has a shape of a cylinder with an outer periphery cut off with two parallel planes and includes a two holding parts 732a and 732b that protrude in parallel. When the driver shaft 713 is inserted into the holding tube 730, the driver part 714 protrudes from between the holding parts 732a and 732b.

When the set-screw-driver 700 is used, the surgeon attaches the set screw 140 to the driver part 714 and clamps the hook 110 between the holding parts 732a and 732b, then screws the set screw 140 into the screw hole 114. Then, the surgeon rotates the T-shaped handle 711 with one hand while supporting the gripping fixed part 720 with the other hand. This rotates the driver shaft 713 and the driver part 714. Since the hook 110 is clamped between the holding parts 732a and 732b and the gripping fixed part 720 is held by the hand, the hook 110 does not rotates along with the T-shaped handle 711 and the set screw 140 is screwed into the screw hole 114 as the T-shaped handle 711 is rotated. When a predetermined torque is reached, the torque management mechanism 712 emits a sound. The surgeon hears the sound, stops rotating the T-shaped handle 711 and finishes the attachment of the set screw 140. A similar operation is performed for the hook 120 and the set screw 150 and the set screw 150 is attached to the hook 120.

A procedure for attaching the transverse 100 to the rods 10 will be described next with reference to FIGS. 12 to 19. The description is given here based on the assumption that pedicle screws 20 have been inserted in a vertebra 30 and the rods 10 have been attached to the pedicle screws 20.

Figure 12:
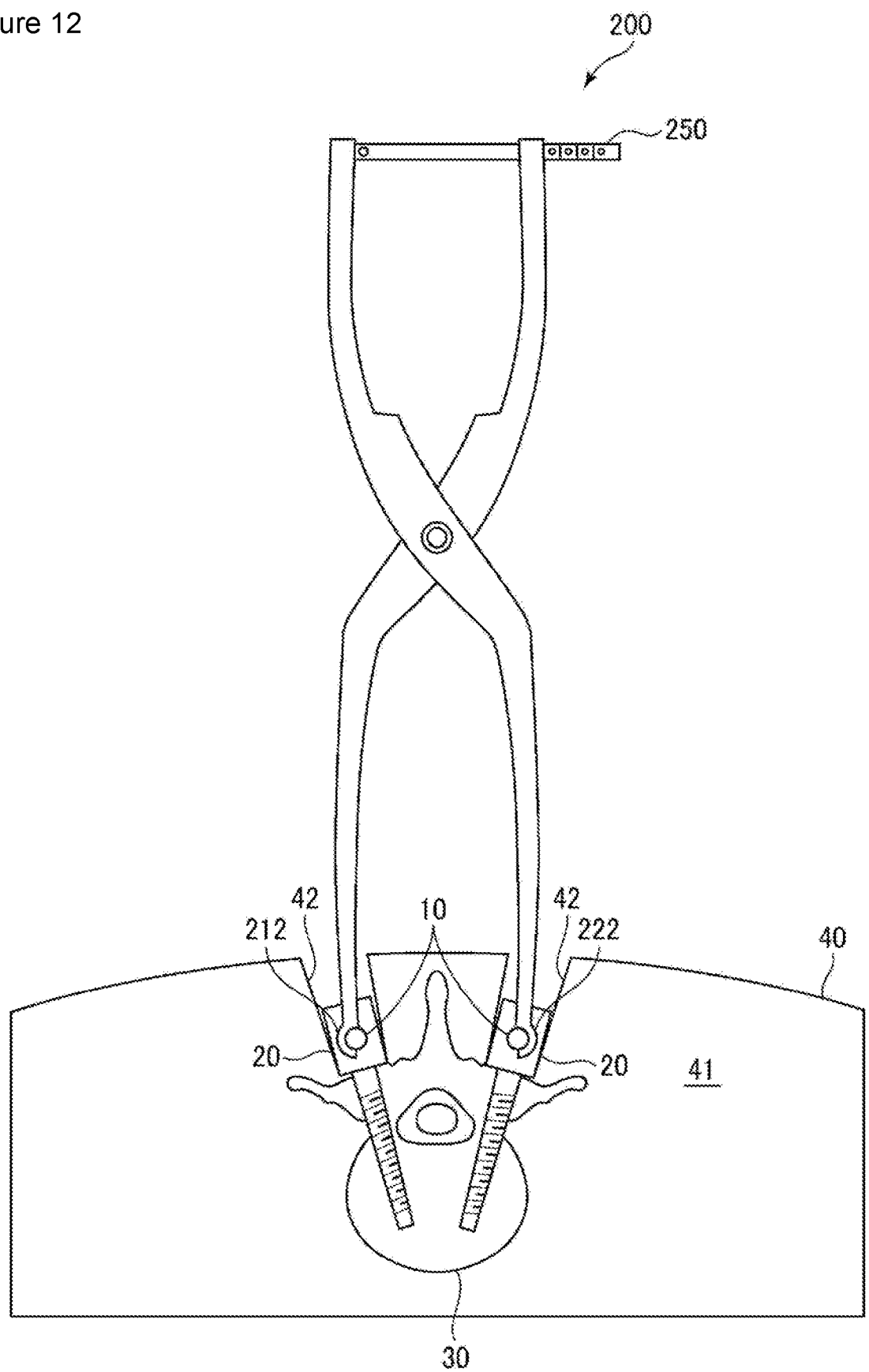
FIG. 12 is a diagram illustrating the step of attaching the sizer to a rod.

A procedure for attaching the sizer 200 to the rods 10 will be described first with reference to FIG. 12. The surgeon grips one end of each of the two sizer bars 210, 220 and inserts the rod gripping ends 212, 222 into holes 42 slightly made in skin 40 and soft tissue 41. When the surgeon grips the end of each of the sizer bars 210, 220 in such a way that the rods 10 engage with the inner peripheries of the rod gripping ends 212, 222, the rods 10 are held at the inner peripheries of the rod gripping ends 212, 222 and the lock 240 works to prevent the rod gripping ends 212, 222 from easily removed from the rods 10. With this, the sizer 200 is attached to the rods 10. After the rod gripping ends 212, 222 grip the rods 10, the surgeon can know the spacing between the two rods 10 by referring to the tick marks on the scale part 250. The surgeon chooses the length of the transverse bar 130 by taking into consideration the spacing between the two rods 10. The sizer 200 can be percutaneously attached to the rods 10 by using the holes 42 without making an incision.

Figure 13:
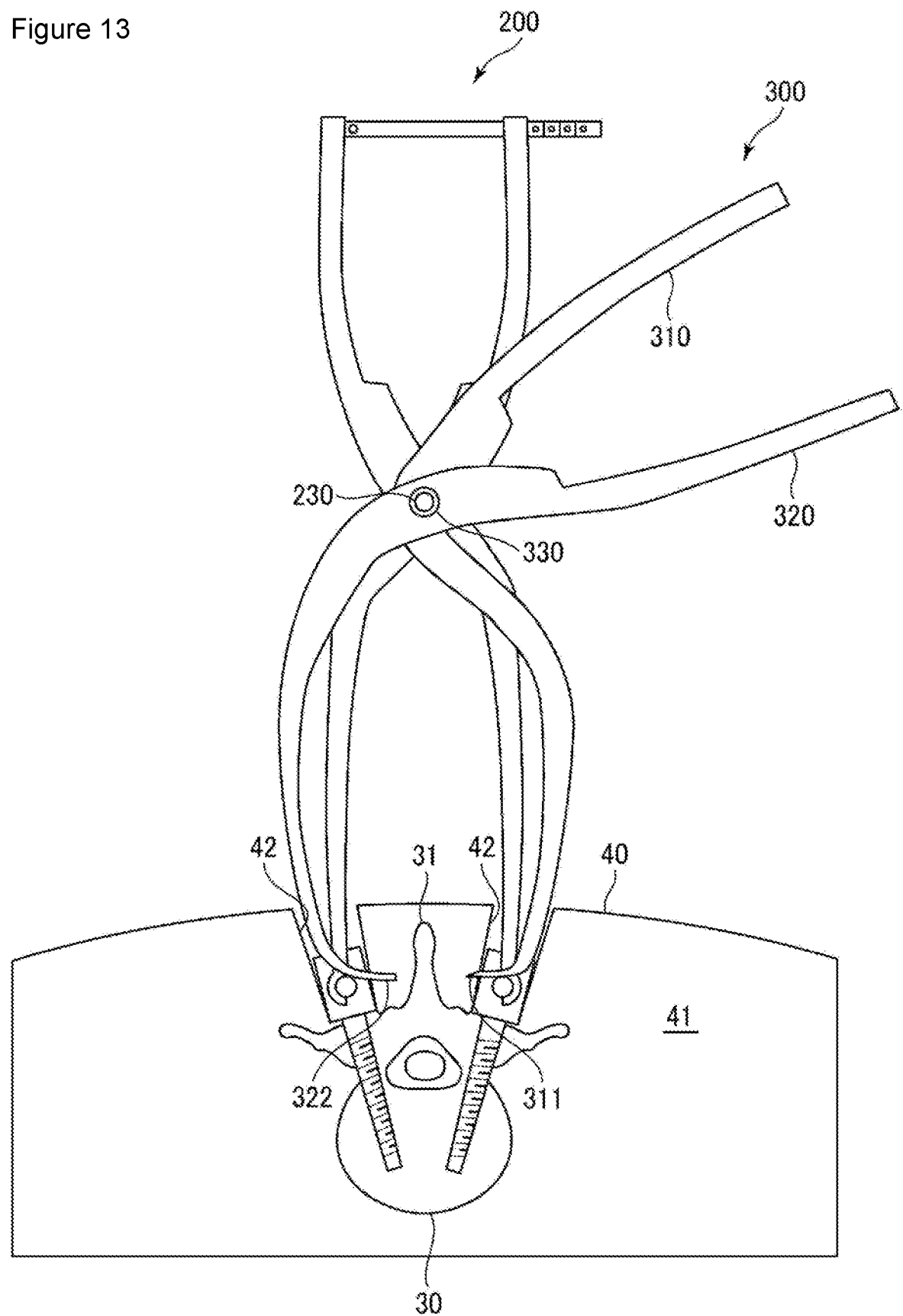
FIG. 13 is a diagram illustrating the step of making a hole in a spinous process.

A procedure for making a hole in a spinous process 31 using the vertebra awl 300 will be described next with reference to FIG. 13.

The surgeon grips the end pars of the first vertebra awl bar 310 and the second vertebra awl bar 320 and inserts the sharp-pointed vertebra awl tip 311 and the vertebra awl recess 322 into the holes 42. The surgeon then inserts the centering shaft 230 into the inner periphery of the hollow shaft 330. The surgeon attaches the nut to the centering shaft 230 to prevent the vertebra awl 300 from moving in the direction of the axis of the centering shaft 230.

Then, when the surgeon grips the ends of the first vertebra awl bar 310 and the second vertebra awl bar 320, the spacing between the sharp-pointed vertebra awl tip 311 and the vertebra awl recess 322 decreases and the sharp-pointed vertebra awl tip 311 and the vertebra awl recess 322 collide with the spinous process 31. When the surgeon further grips the ends of the first vertebra awl bar 310 and the second vertebra awl bar 320, the sharp-pointed vertebra awl tip 311 and the vertebra awl recess 322 pass into the spinous process 31 to make a hole 32 (see FIG. 14). Since the distance from the axis of the centering shaft 230 to the tip of the sharp-pointed vertebra awl tip 311 has been predetermined in accordance with the position of the hole to be made in the spinous process 31 of the vertebra 30, the surgeon can easily make the hole 32 in a proper position simply by gripping the ends of the first vertebra awl bar 310 and the second vertebra awl bar 320.

When the surgeon realizes that the sharp-pointed vertebra awl tip 311 and the vertebra awl recess 322 have contacted each other through a feel in the hand, the surgeon operates the ends of the first vertebra awl bar 310 and the second vertebra awl bar 320 to widen the spacing between the sharp-pointed vertebra awl tip 311 and the vertebra awl recess 322. The surgeon then removes the nut from the centering shaft 230 and removes the vertebra awl 300 from the centering shaft 230. This ends the procedure for making the hole 32 in the spinous process 31 using the vertebra awl 300. By using the vertebra awl 300, the hole 32 can be percutaneously made in the spinous process 31 without making an incision (see FIG. 14).

Figure 14:
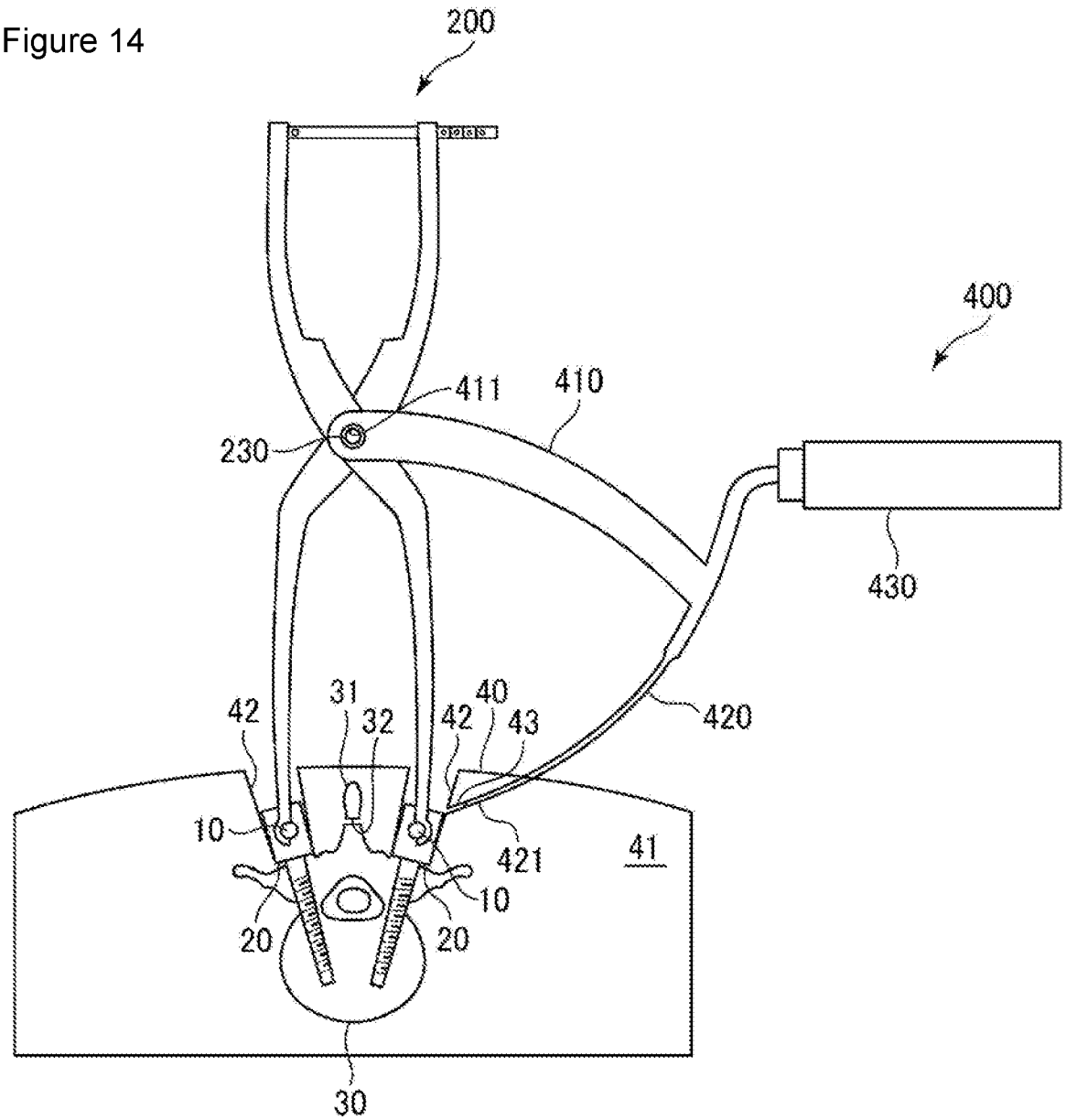
FIG. 14 is a diagram illustrating the step of making a hole in soft tissue.

A procedure for making a through-hole 43 in skin 40 and soft tissue 41 using the soft-tissue awl 400 will be described next with reference to FIG. 14.

The surgeon inserts the centering shaft 230 into the inner periphery of the hole 411. The surgeon then attaches the nut to the centering shaft 230 to prevent the soft-tissue awl 400 from moving in the direction of the axis of the centering shaft 230. Then, the surgeon inserts the soft-tissue insertion sharp-pointed tip 421 into the skin 40 and the soft tissue 41 by gripping the awl handle 430. After inserting the soft-tissue insertion sharp-pointed tip 421 until a hole 42 is reached, the surgeon pulls the soft-tissue insertion sharp-pointed tip 421 out of the skin 40 and the soft tissue 41 by operating the awl handle 430.

As described previously, the curvature of the penetrator 420 is equal to the curvature of the transverse bar 130 and the distance from the axis of the centering shaft 230 to the soft-tissue insertion sharp-pointed tip 421 has been determined in accordance with the position in which the transverse bar 130 is to be provided. Accordingly, the curvature of the through-hole 43 is equal to the curvature of the transverse bar 130 and the position of the through-hole 43 is a position that continues to the position in which the transverse bar 130 is provided when the transverse bar 130 is inserted into the through-hole 43.

After pulling out the soft-tissue insertion sharp-pointed tip 421, the surgeon removes the nut from the centering shaft 230 and removes the soft-tissue awl 400 from the centering shaft 230. This ends the procedure for making the through-hole 43 in the soft tissue 41 using the soft-tissue awl 400. By using the soft-tissue awl 400, the through-hole 43 can be made percutaneously in the soft tissue 40 without making an incision.

Figure 15:
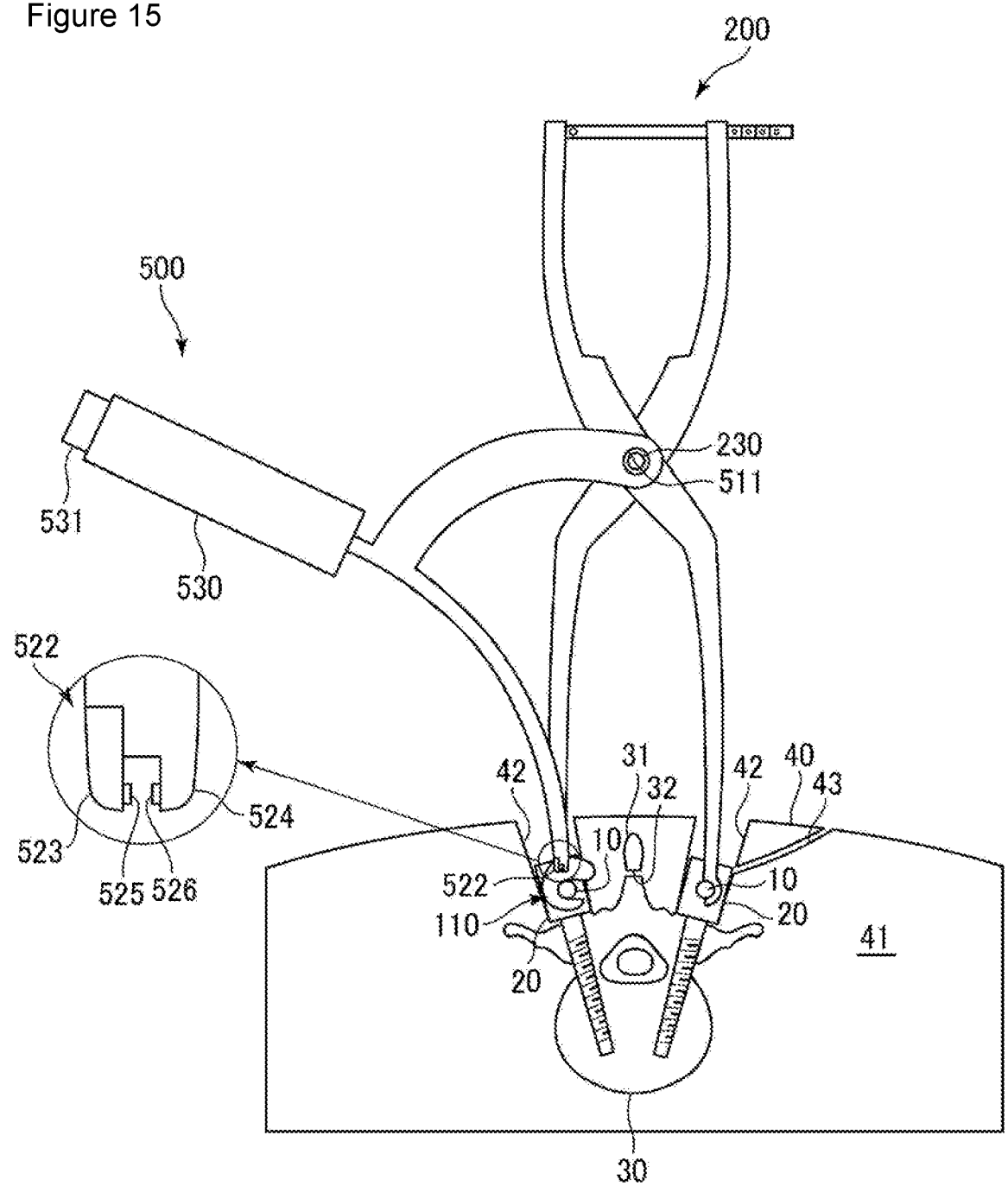
FIG. 15 is a diagram illustrating the step of attaching a hook to a rod.

A procedure for attaching a hook 110 to a rod 10 using the hook holder 500 will be described next with reference to FIG. 15.

The surgeon opens the movable part 523 by rotating the hook operating part 531. The surgeon then places the hook 110 between the movable part 523 and the fixed part 524 in such a way that the protrusion 525 and the protrusion 526 fit into the two hook-holder-receiving recesses 115, 125, respectively, and rotates the hook operating part 531 to close the movable part 523. This fixes the hook 110 to the hook gripping part 522.

Then, the surgeon grips the hook holder handle 530 and inserts the hook gripping part 522 and the hook 110 into a hole 42. The surgeon then inserts the centering shaft 230 into the inner periphery of the hole 511. Then, the surgeon attaches the nut to the centering shaft 230 to prevent the hook holder 500 from moving in the direction of the axis of the centering shaft 230. The surgeon then turns the hook holder 500 around the axis of the centering shaft 230 by operates the hook holder handle 530 to attach the hook 110 to the rod 10. As described previously, the distance from the bar hole 111 of the hook 110 attached to the hook gripping part 522 to the axis of the centering shaft 230 has been determined in accordance with the positional relationship between the axis of the centering shaft 230 and the rod 10. Accordingly, the rod 10 enters the bar hole 111 and the hook 110 is attached to the rod 10 simply by turning the hook holder 500 around the axis of the centering shaft 230. This ends the procedure for attaching the hook 110 to the rod 10 using the hook holder 500. By using the hook holder 500, the hook 110 can be percutaneously attached to the rod 10 through the hole 42 without making an incision.

Figure 16:
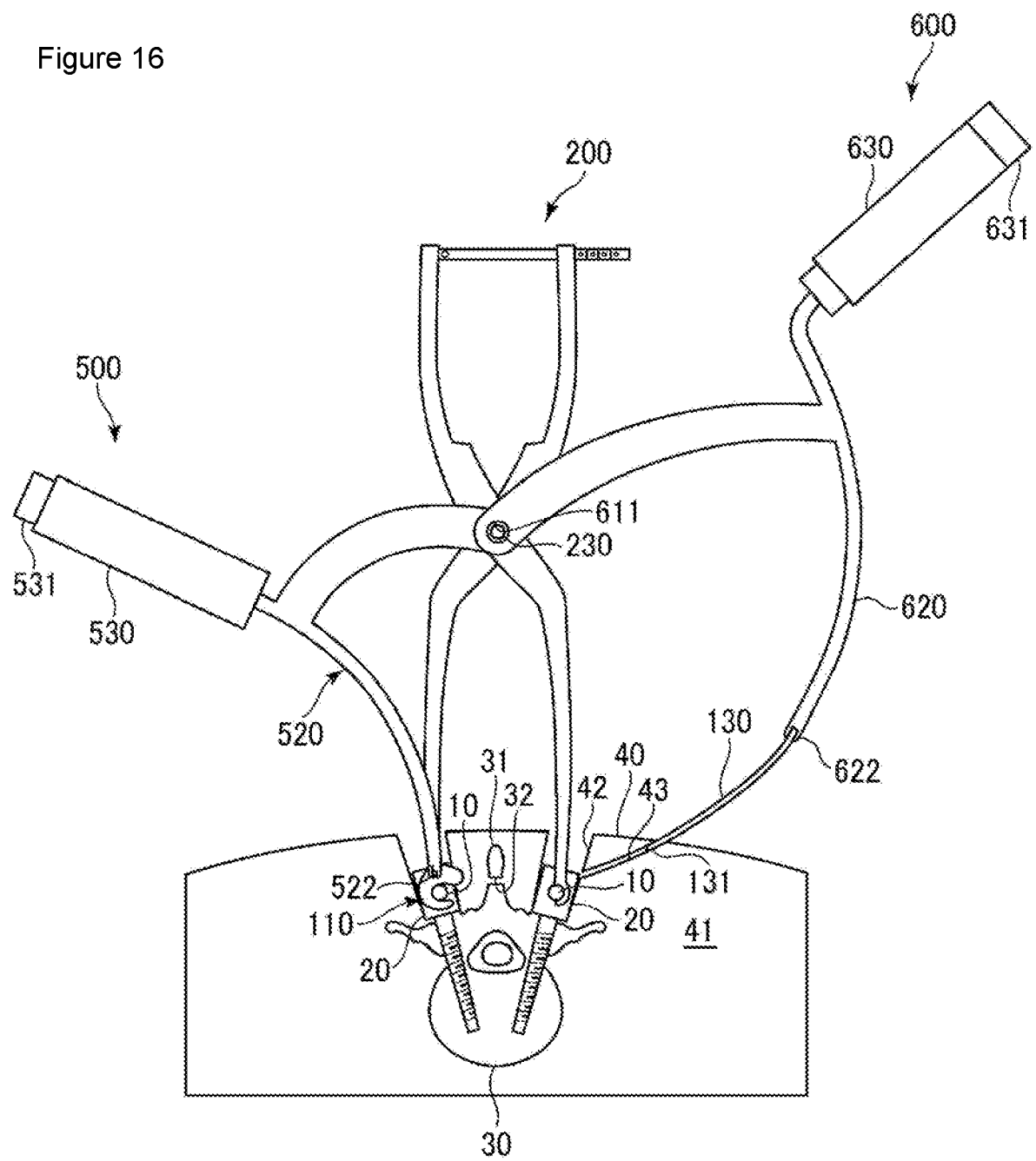
FIG. 16 is a diagram illustrating the step of inserting a transverse bar.
Figure 17:
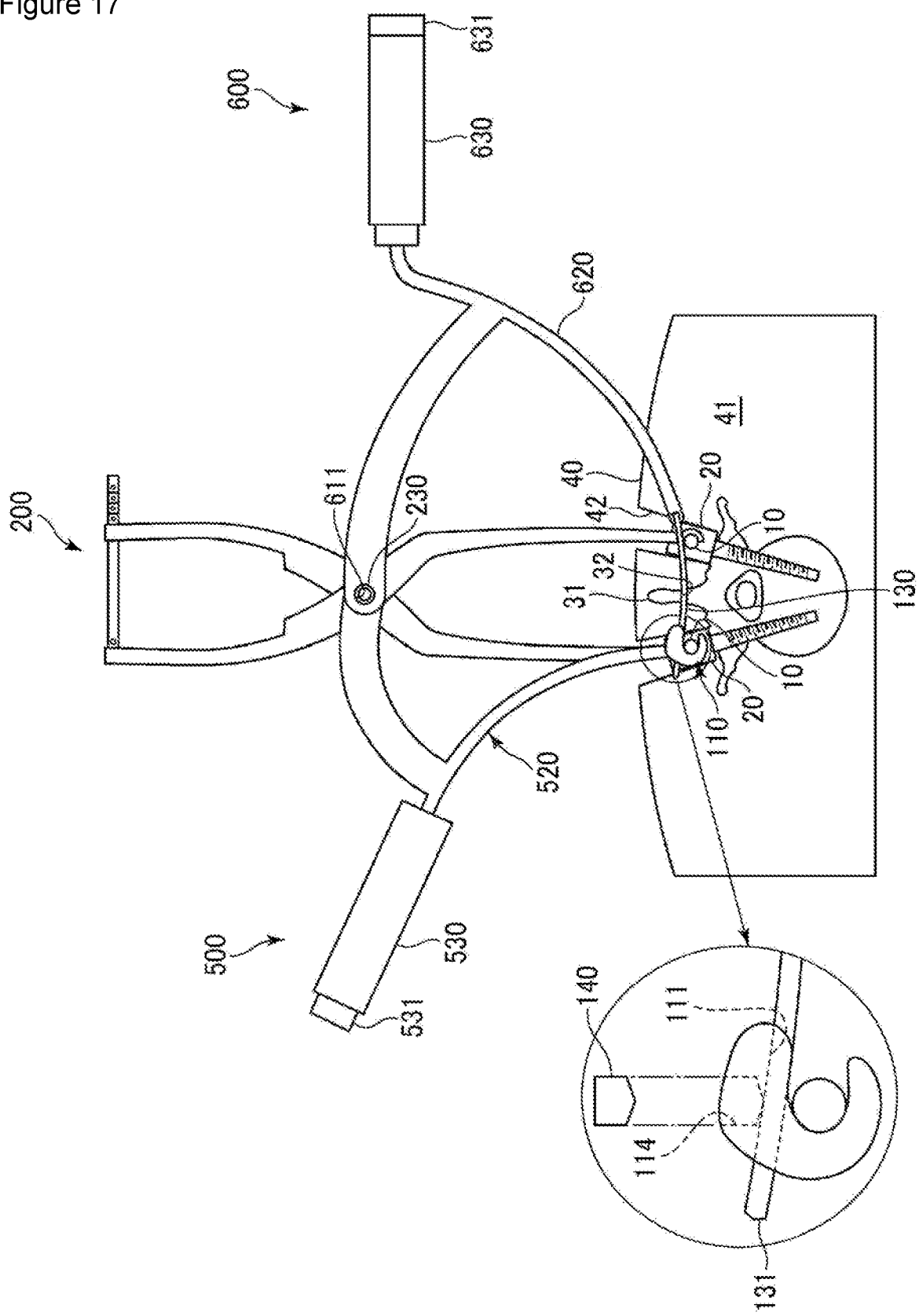
FIG. 17 is a diagram illustrating the step of temporarily fixing the transverse bar and other elements using a set screw.

A procedure for passing the transverse bar 130 through soft tissue 41, a hole 32 and a hook 110 using the bar holder 600 will be described next with reference to FIGS. 16 and 17.

As described previously, the surgeon has chosen the length of the transverse bar 130 by referring to the scale part 250 of the sizer 200. The surgeon attaches the transverse bar 130 having the chosen length to the holder 600. Specifically, the surgeon rotates the bar operating part 631 to widen the spacing between the movable part 623 and the fixed part 624. Then, the surgeon places the transverse bar 130 between the movable part 623 and the fixed part 624 and rotates the bar operating part 631 to close the movable part 623. This fixes the transverse bar 130 to the bar gripping part 622.

Then, the surgeon inserts the centering shaft 230 into the inner periphery of the hole 611. The surgeon then attaches the nut to the centering shaft 230 to prevent the bar holder 600 from moving in the direction of the axis of the centering shaft 230. The surgeon then grips the bar holder handle 630 and inserts the transverse bar 130 into the through-hole 43 while turning the bar holder 600 around the axis of the centering shaft 230. The surgeon further turns the bar holder 600 around the axis of the centering shaft 230 to cause the transverse bar 130 to enter the hole 32 and the bar hole 111. As described previously, the curvature of the bar gripping part 622 is equal to the curvature of the transverse bar 130 and the distance from the bar gripping part 622 to the axis of the centering shaft 230 has been determined so as to be equal to the distance between the axis of the centering shaft 230 and the hole 32 when the sizer 200 is fixed to the rod 10. Accordingly, the transverse bar 130 can easily enter the through-hole 43, the hole 32, and the bar hole 111 without resistance from the soft tissue 41, the spinous process 31, and the hook 110 simply by turning the bar holder 600 around the axis of the centering shaft 230 (see FIG. 17). This ends the procedure for passing the transverse bar 130 through the soft tissue 41, the hole 32 and the hook 110 using the bar holder 600. By using the bar holder 600, the transverse bar 130 can be percutaneously passed through the soft tissue 41, the hole 32 and the hook 110 without making an incision.

A procedure for temporarily fixing the transverse bar 130 to a hook 110 and a rod 10 using the set screw 140 will be described next with reference to FIGS. 11 and 17.

After checking that the transverse bar 130 has completely passed through the bar hole 111, the surgeon attaches the set screw 140 to the set-screw-driver 700, inserts the tip 731 into the hole 42, clamps the hook 110 between the holding parts 732a and 732b, then screws the set screw 140 into the screw hole 114. The surgeon then rotates the T-shaped handle 711 with one hand while supporting the gripping fixed part 720 with the other hand. Since the hook 110 is clamped between the holding parts 732a and 732b and the gripping fixed part 720 is held by the hand, the hook 110 does not rotates along with the T-shaped handle 711 and the set screw 140 is screwed into the screw hole 114 as the T-shaped handle 711 is rotated. Here, the set screw 140 is screwed into the screw hole 114 until the set screw 140 lightly contacts the transverse bar 130 rather than screwing the set screw 140 into the screw hole 114 until a predetermined torque is reached. This ends the procedure for temporarily fixing the transverse bar 130 to the hook 110 and the rod 10 using the set screw 140. By using the hole 42, the set screw 140 can be percutaneously screwed into the screw hole 114 without making an incision.

Figure 18:
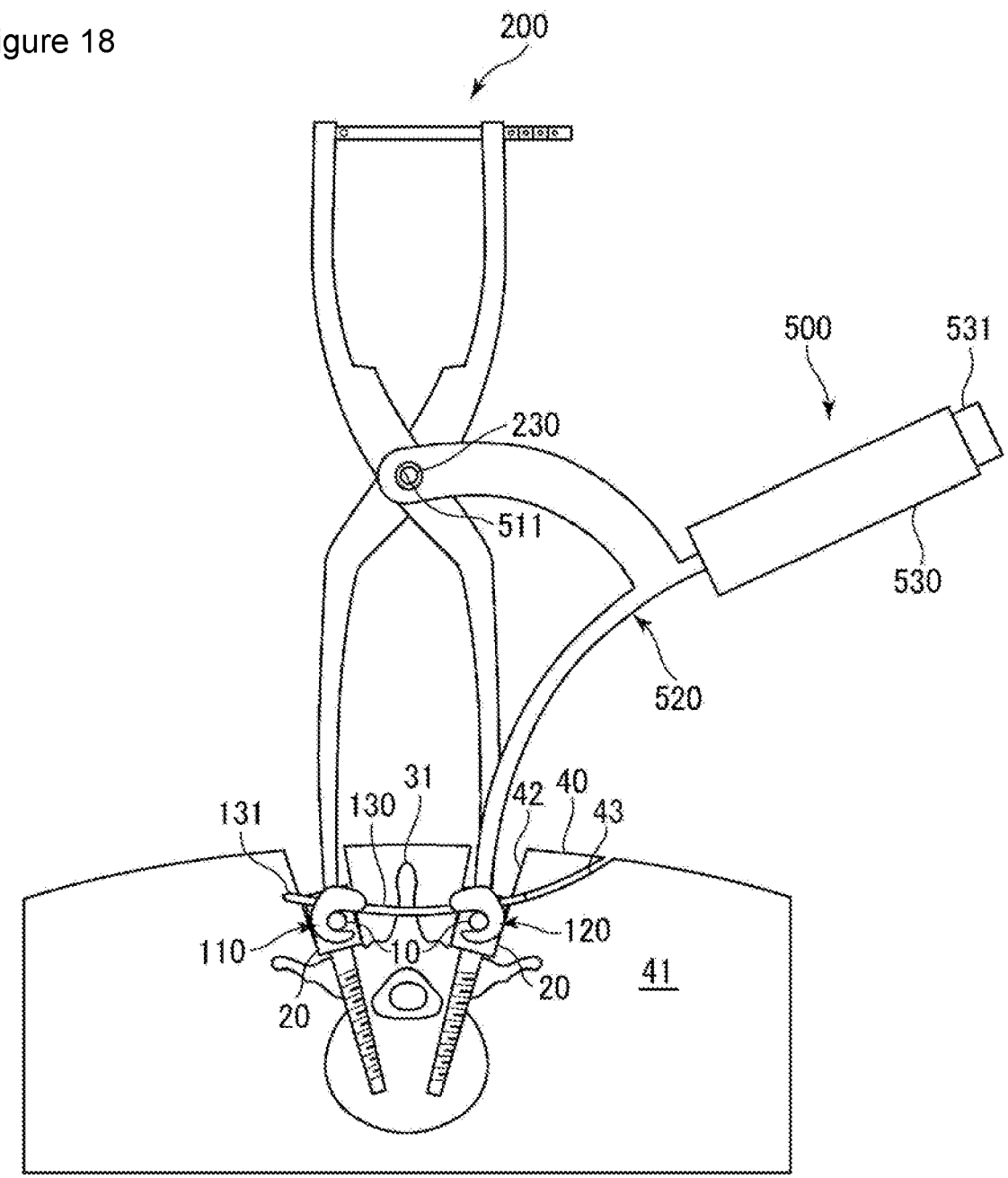
FIG. 18 is a diagram illustrating the step of attaching a hook to a rod.

A procedure for attaching the hook 120 to the rod 10 and the transverse bar 130 using the hook holder 500 will be described next with reference to FIG. 18.

The surgeon fixes the hook 120 to the hook gripping part 522 by operating the hook operating part 531 in the same manner described previously. The surgeon then grips the hook holder handle 530 and inserts the hook gripping part 522 and the hook 120 into a hole 42. Then, the surgeon attaches the hook holder 500 to the centering shaft 230 in the same manner described previously. The surgeon then operates the hook holder handle 530 to turn the hook holder 550 around the axis of the centering shaft 230, thereby attaching the hook 120 to the transverse bar 130 and the rod 10. As described previously, the distance from the bar hole 121 of the hook 120 attached to the hook gripping part 522 to the axis of the centering shaft 230 has been determined in accordance with the positional relationship between the axis of the centering shaft 230 and the rod 10. Accordingly, the rod 10 enters the bar hole 121 and the hook 120 is attached to the rod 10 simply by turning the hook holder 500 around the axis of the centering shaft 230.

Then, after checking that the transverse bar 130 has completely passed through the bar hole 121, the surgeon screws the set screw 150 into the screw hole 124 using the set-screw-driver 700 until the set screw 140 lightly contacts the transverse bar 130 by following the same procedure described previously. This ends the procedure for attaching the hook 120 to the rod 10 using the hook holder 500. By using the hook holder 500, the hook 120 can be percutaneously attached to the rod 10 and the transverse bar 130 through the hole 42 without making an incision.

Figure 19:
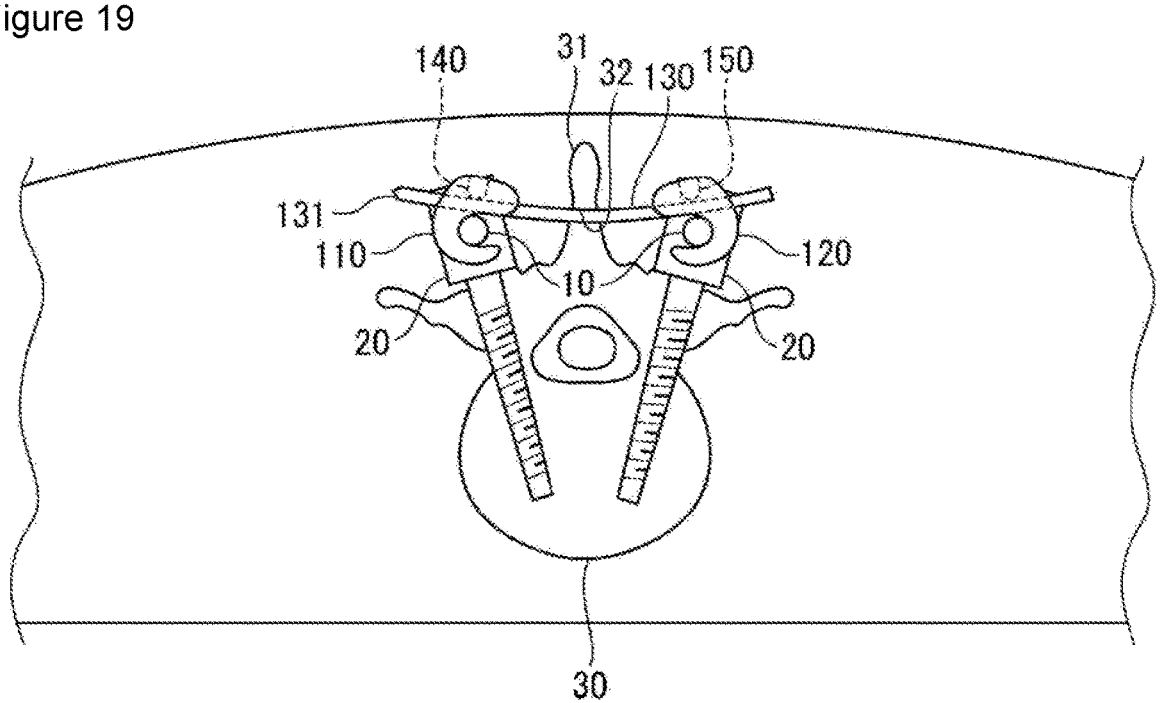
FIG. 19 is a diagram illustrating the transverse attached to rods.

A procedure for ultimately fastening the set screws 140, 150 will be described next with reference to FIGS. 11 and 19.

After clamping the hook 110 between the holding parts 732a and 732b, the surgeon fits the set screw 140 into the driver part 714 of the set-screw-driver 700 and rotates the T-shaped handle 711 with one hand while supporting the gripping fixed part 720 with the other hand. Since the hook 110 is clamped between the holding parts 723a and 732b and the gripping fixed part 720 is held with the hand, the hook 110 does not rotates along with the T-shaped handle 711 and the screw 140 is screwed into the screw hole 114 as the T-shaped handle 711 is rotated. When a predetermine torque is reached, the torque management mechanism 712 emits a sound. The surgeon hears the sound and stops rotating the T-shaped handle 711. At this point of time, the set screw 140 presses the transverse bar 130, thereby restraining the transverse bar 130 in the longitudinal direction. Since a portion of the bar hole 111 adjoins the rod opening 113, the pressed transverse bar 130 contacts the rod 10 and pushes the rod 10 against the rod opening 113. Then, the protrusion 127 engages with the rod 10 to restrain the hook 110 in the longitudinal direction and circumferential direction of the rod 10. This ultimately fastens the set screw 140. The set screw 150 is also ultimately fastened by the same method. This ends the procedure for ultimately fastening the set screws 140, 150. By using the torque management mechanism 712, the transverse 100 can be reliably fixed to the rod 10 without harming the vertebra and without loose of the set screw 140.

According to the present embodiment, the transverse 100 can be percutaneously installed in minimally invasive surgery.

Since the transverse bar 130 passes inside the hole 32 provided in the spinous process 31, the transverse 100 is fixed in the direction in which the vertebra 30 protrudes. When a pedicle screw is attached to a vertebra of a patient with osteoporosis, the pedicle screw may not work and can come off the vertebra because of fragile bone. However, in the present embodiment, the pedicle screw 20 does not come off the vertebra 30 even if a force in the direction in which the vertebra 30 protrudes, that is, a force that would cause the pedicle screw 20 to come off the vertebra 30, is exerted on the pedicle screw 20, because the transverse 100 is fixed in the direction in which the vertebra 30 protrudes.

It should be noted that in the procedure for making a hole in the spinous process 31 using the vertebra awl 300, the centering shaft 230 may be inserted into the inner periphery of the hollow shaft 330 before inserting the sharp-pointed vertebra awl tip 311 and the vertebra awl recess 322 into the holes 42.

Similarly, in the procedure for making a through-hole 43 in the skin 40 and the soft tissue 41 using the soft-tissue awl 400, the soft-tissue insertion sharp-pointed tip 421 may be inserted to some degree into the skin 40 and the soft tissue 41 before inserting the centering shaft 230 into the inner periphery of the hole 411.

Further, in the procedure for attaching the hook 110 to the rod 10 using the hook holder 500, the centering shaft 230 may be inserted into and fixed to the inner periphery of the hole 511 before inserting the hook gripping part 522 and the hook 110 into the hole 42.

Further, in the procedure for passing the transverse bar 130 through the soft tissue 41, the hole 32 and the hook 110 using the bar holder 600, the transverse bar 130 may be inserted to some degree into the through-hole 43 before inserting and fixing the centering shaft 230 to the inner periphery of the hole 611.

Further, in the procedure for attaching the hook 120 to the rod 10 and the transverse bar 130 using the hook holder 500, the hook holder 500 may be attached to the centering shaft 230 before inserting the hook gripping part 522 and the hook 120 into the hole 42.

It should be noted that the predetermined curvature is not limited to the value given previously. The lengths of varieties of the transverse bar are not limited to the values given above and the number of lengths of the varieties of the transverse bar is not limited to six.

It should be noted that the value of the tick mark on the scale part 250 indicated by the edge of the hole 241 may be the distance between the axes of the two rods 10, the distance between the outer sides of the two rods 10, or the length of a transverse bar 130 to be used, rather than the spacing between the two rods 10.

It should be noted that the lock 240 is not limited a lock 240 that uses a hole 241 but may be a lock 240 that uses a frictional resistance or the like provided between the hole 221 and the centering shaft 230 to mechanically fix the sizer bar 210 to the sizer bar 220.

It should be noted that the soft-tissue awl 400 does not always need to be used. The soft-tissue awl 400 may be used to make a through-hole in soft tissue 41 only when soft tissue 41 is so thick that the transverse bar 130 cannot easily be inserted through the hole 42.

It should be noted that numbers indicating the size of the transverse 100 in drawings are illustrative and the size of the transverse 100 according to the present invention is not limited to these values.

It should be noted that numbers indicating the sizes of members in the description and drawings are illustrative and the sizes are not limited to these values.

While embodiments of the present invention have been described herein with reference to the accompanying drawings, it will be obvious to those skilled in the art that modifications can be made to structures of components and relationships between the components without departing from the scope and spirit of the present invention described.

The invention claimed is:

1. A surgical instrument used for attaching a transverse coupler, the surgical instrument comprising:
   a sizer comprising:
      two sizer bars;
      a centering shaft rotatably supporting the two sizer bars on a predetermine axis; and
      a lock preventing rotation of the sizer bars with respect to the centering shaft;
      wherein a rod gripping end is provided at one end of each of the sizer bars, so that each gripping end engages with a rod that couples screws configured to be inserted in vertebrae;
   a vertebra awl comprising:
      at least one vertebra awl bar equipped with a sharp-pointed vertebra awl tip configured to make a hole in the vertebra at one end of the vertebra awl bars; and
      wherein the centering shaft rotatably supports the vertebra awl bar on the predetermined axis;
      wherein the centering shaft is coaxial with the predetermined axis; and
   a hook holder comprising:
      a hook holder extended rod rotationally supported at one end by the predetermined axis and radially extending from the predetermined axis; and
      a hook holder arm extending from another end of the hook holder extended rod;
      wherein a hook gripper configured to grip at least one of the plurality of hooks is provided at a tip of the hook holder arm, and
   a bar holder comprising:
      a bar holder extended rod rotatably supported at one end by the predetermined axis and radially extending from the predetermined axis; and
      a bar holder arm having a predetermined curvature and extending from another end of the bar holder extended rod;
      wherein a bar gripper configured to grip a transverse bar is provided at a tip of the bar holder arm;
      wherein the bar holder includes a release mechanism for releasing gripping of the bar gripper to install the transverse bar in a predetermined position after the transverse bar penetrates into a body and is installed in a predetermined position;
   wherein the transverse coupler comprises:
      a plurality of hooks engaging with a rod that couples screws, wherein each of the screws is configured to be inserted in a vertebra; and
      a transverse bar having a predetermined curvature and provided between the plurality of hooks;
      wherein the plurality of hooks includes a bar hole through which the transverse bar passes, a screw hole that communicates with the bar hole and a rod opening that engages with the rod;
      wherein the bar hole communicates with the rod opening;
      wherein the transverse coupler further includes a set screw configured to be screwed in the screw hole; and
      wherein when the set screw enters the screw hole, a tip of the set screw engages with and presses the transverse bar and the transverse bar pressed by the tip of the set screw presses the rod and pushes the rod against the rod opening.

2. A transverse installer for installing in a body a transverse coupler including a rod-shaped transverse coupling bar having a predetermined curvature in a longitudinal direction, the transverse coupler being an instrument used for transversely coupling at least two vertical couplers provided in order to vertically settle a spine by coupling screws inserted in vertebrae of the spice,
   the transverse installer comprising a positioning device for determining a position in which the transverse coupler is to be inserted and installed, and transverse insertion and installation tool percutaneously inserting and installing the transverse coupler,
   wherein the positioning devices comprises:
   at least two sizer bars and a mechanism that positions and attaches the at least two sizer bars in a predetermined position on each of the at least two vertical couplers before installation of the transverse coupler, and that releases the sizer bars from the vertical couplers after the installation of the transverse coupler;
   the transverse insertion and installation tool comprises:
   a penetrator that penetrates into a body;
   a mechanism allowing the penetrator to move along an arc having a curvature substantially equal to the curvature when the penetrator penetrates into the body; and
   a fixing mechanism that fixes the arc in a position that is fixed relative to the positioning device during the movement; and
   the transverse installer enables the rod-shaped transverse coupling bar to percutaneously penetrate and be percutaneously installed along at least a portion of the arc;
   wherein the transverse insertion and installation tool comprises a vertebra awl including:
   at least one vertebra awl bar being an extended rod; and
   a centering shaft rotatably supporting the vertebra awl bar on a predetermined axis; and
   a penetrator being a sharp-pointed vertebra awl tip configured to make a hole in the vertebra at one end of the vertebra awl bar.

3. A transverse installer for installing in a body a transverse coupler including a rod-shaped transverse coupling bar having a predetermined curvature in a longitudinal direction, the transverse coupler being an instrument used for transversely coupling at least two vertical couplers provided in order to vertically settle a spine by coupling screws inserted in vertebrae of the spine, the transverse installer comprising a positioning device for determining a position in which the transverse coupler is to be inserted and installed, and transverse insertion and installation tool percutaneously inserting and installing the transverse coupler, wherein the positioning device comprises:

at least two sizer bars and a mechanism that positions and attaches the at least two sizer bars in a predetermined position on each of the at least two vertical couplers before installation of the transverse coupler, and that releases the sizer bars from the vertical couplers after the installation of the transverse coupler;

the transverse insertion and installation tool comprises:

a penetrator that penetrates into a body;

a mechanism allowing the penetrator to move along an arc having a curvature substantially equal to the curvature when the penetrator penetrates into the body; and a fixing mechanism that fixes the arc in a position that is fixed relative to the positioning device during the movement; and the transverse installer enables the rod-shaped transverse coupling bar to percutaneously penetrate and be percutaneously installed along at least a portion of the arc;

wherein the transverse insertion and installation tool comprises a bar holder including:

a bar holder extended rod rotatably supported at one end by a predetermined axis and radially extending from the predetermined axis; and a bar holder arm having a predetermined curvature and extending from another end of the bar holder extended rod;

a bar gripper gripping a transverse coupling bar as a penetrator is provided at a tip of the bar holder arm; and the bar holder includes a release mechanism for releasing gripping of the bar gripper to install the rod-shaped transverse coupling bar in a predetermined position after the rod-shaped traverse coupling bar penetrates into and is installed in a predetermined position.

4. A transverse installer for installing in a body a transverse coupler, the transverse installer being an instrument for percutaneously installing a transverse coupler in a body, including a rod-shaped transverse coupling bar having a predetermined curvature in a longitudinal direction, the transverse coupler being an instrument used for transversely coupling at least two vertical couplers provided in order to vertically settle a spice by coupling screws inserted in vertebrae of the spine, the transverse installer comprising a positioning device for determining a position in which the transverse coupler is to be inserted and installed, and transverse insertion and installation tool percutaneously inserting and installing the transverse coupler, wherein the positioning device comprises:

at least two sizer bars and a mechanism that positions and attaches the at least two sizer bars in a predetermined position on each of the al least two vertical couplers before installation of the transverse coupler, and that releases the sizer bars from the vertical couplers after the installation of the transverse coupler;

the transverse insertion and installation tool comprises;

a penetrator that penetrates into a body;

a mechanism allowing the penetrator to move along an arc having a curvature substantially equal to the curvature when the penetrator penetrates into the body; and a fixing mechanism that fixes the arc in a position that is fixed relative to the positioning device during the movement; and the transverse installer enables the rod-shaped transverse coupling bar to percutaneously penetrate and be percutaneously installed along at least a portion of the arc;

wherein the transverse coupler includes a transverse coupling bar; and a hook that engages with the rod to fix the transverse coupling bar; and the transverse installer comprises a mechanism that positions the hook relative to the positioning device when the rod-shaped transverse coupling bar inserted and installed along the arc by the transverse insertion and installation tool is fixed to the rod.

5. The transverse installer according to claim 4, comprising a hook holder as the mechanism positioning the hook relative to the positioning device, wherein the hook holder comprises:

a hook holder extended rod rotatably supported at one end by a predetermined axis and radially extending from the predetermined axis; and a hook holder arm extending from another end of the hook holder extended rod;

a hook gripper configured to grip a hook is provided at a tip of the hook holder arm; and the hook is movable along the arc along which the rod-shaped transverse coupling bar moves or an arc extending from the arc.

6. The transverse installer according to claim 4, wherein the hook includes a bar hole through which the rod-shaped transverse coupling bar passes and a rod opening that engages with the rod, and the bar hole communicates with the rod opening.

7. The transverse installer according to claim 6, wherein the hook includes a screw hole communicating with the bar hole;

the transverse coupler further includes a set screw configured to be screwed into the screw hole; and when the set screw enters the screw hole, a tip of the set screw engages with the rod-shaped transverse coupling bar to press the rod-shaped transverse coupling bar and the rod-shaped transverse coupling bar pressed by the tip of the set screw presses the rod to push the rod against the rod opening.

8. A transverse installer for installing in a body a transverse coupler including a rod-shaped transverse coupling bar having a predetermined curvature in a longitudinal direction, the transverse coupler being an instrument used for transversely coupling at least two vertical couplers provided in order to vertically settle a spine by coupling screws inserted in vertebrae of the spine, the transverse installer comprising a positioning device for determining a position in which the transverse coupler is to be inserted and installed, and transverse insertion and installation tool percutaneously inserting and installing the transverse coupler, wherein the positioning device comprises:

at least two sizer bars and a mechanism that positions and attaches the at least two sizer bars in a predetermined position on each of the at least two vertical couplers before installation of the transverse coupler, and that releases the sizer bars from the vertical couplers after the installation of the transverse coupler;

the transverse insertion and installation tool comprises:
a penetrator that penetrates into a body;
a mechanism allowing the penetrator to move along an arc having a curvature substantially equal to the curvature when the penetrator penetrates into the body; and
a fixing mechanism that fixes the arc in a position that is fixed relative to the positioning device during the movement; and
the transverse installer enables the rod-shaped transverse coupling bar to percutaneously penetrate and be percutaneously installed along at least a portion of the arc;
wherein the transverse insertion and installation tool comprises:
a vertebra awl including at least one vertebra awl bar as an extended rod, and a centering shaft rotatably supporting the vertebra awl bar on a predetermined axis, one end of the vertebra awl bar including a penetrator being a sharp-pointed vertebra awl tip configured to make a hole in the vertebra; and
a bar holder including a bar holder extended rod rotatably supported at one end by a predetermined axis and radially extending from the predetermined axis, and a bar holder arm having a predetermined curvature and extending from another end of the bar holder extended rod,
wherein a bar gripper gripping a transverse coupling bar as a penetrator is provided at a tip of the bar holder arm, and the bar holder includes a release mechanism for releasing gripping of the bar gripper to install the rod-shaped transverse coupling bar in a predetermined position after the rod-shaped transverse coupling bar penetrates into and is installed in a predetermined position.

9. A transverse installer for installing in a body a transverse coupler including a rod-shaped transverse coupling bar having a predetermined curvature in a longitudinal direction, the transverse coupler being an instrument used for transversely coupling at least two vertical couplers provided in order to vertically settle a spine by coupling screws inserted in vertebrae of the spine,
the transverse installer comprising a positioning device for determining a position in which the transverse coupler is to be inserted and installed, and transverse insertion and installation tool percutaneously inserting and installing the transverse coupler,
wherein the positioning device comprises:
at least two sizer bars and a mechanism that positions and attaches the at lease two sizer bars in a predetermined position on each of the at least two vertical couplers before installation of the transverse coupler, and that releases the sizer bars from the vertical couplers after the installation of the transverse coupler;
the transverse insertion and installation tool comprises:
a penetrator that penetrates into a body;
a mechanism allowing the penetrator to move along an arc having a curvature substantially equal to the curvature when the penetrator penetrates into the body; and
a fixing mechanism that fixes the arc in a position that is fixed relative to the positioning device during the movement; and
the transverse installer enables the rod-shaped transverse coupling bar to percutaneously penetrate and be percutaneously installed along at least a portion of the arc;
wherein the transverse insertion and installation tool comprises:
a vertebra awl including at least one vertebra awl bar as an extended rod, and a centering shaft rotatably supporting the vertebra awl bar on a predetermined axis, one end of the vertebra awl bar including a penetrator being a sharp-pointed vertebra awl tip configured to make a hole in the vertebra; and
a soft-tissue awl including an awl extended rod rotatably supported at one end by a predetermined axis and radially extending from the predetermined axis and the penetrator having a predetermined curvature and extending from another end of the awl extended rod, wherein a sharp-pointed soft-tissue awl tip configured to make a hole in soft tissue is provided at a tip of the penetrator.

10. A transverse installer for installing in a body a transverse coupler including a rod-shaped transverse coupling bar having a predetermined curvature in a longitudinal direction, the transverse coupler being an instrument used for transversely coupling at least two vertical couplers provided in order to vertically settle a spine by coupling screws inserted in vertebra of the spine,
the transverse installer comprising a positioning device for determining a position in which the transverse coupler is to be inserted and installed, the transverse insertion and installation tool percutaneously inserting and installing the transverse coupler,
wherein the positioning device comprises:
at least two sizer bars and a mechanism that positions and attaches the at lease two sizer bars in a predetermined position on each of the at least two vertical couplers before installation of the transverse coupler, and that releases the sizer bars from the vertical couplers after the installation of the transverse coupler;
the transverse insertion and installation tool comprises:
a penetrator that penetrates into a body;
a mechanism allowing the penetrator to move along an arc having a curvature substantially equal to the curvature when the penetrator penetrates into the body; and
a fixing mechanism that fixes the arc in a position that is fixed relative to the positioning device during the movement; and
the transverse installer enables the rod-shaped transverse coupling bar to percutaneously penetrate and be percutaneously installed along at least a portion of the arc;
wherein the transverse insertion and installation tool comprises:
a soft-tissue awl including an awl extended rod rotatably supported at one end by a predetermined axis and radially extending from the predetermined axis and the penetrator having a predetermined curvature and extending from another end of the awl extended rod, wherein a sharp-pointed soft-tissue awl tip configured to make a hole in soft tissue is provided at a tip of the penetrator; and
a bar holder including a bar holder extended rod rotatably supported at one end by a predetermined axis and radially extending from the predetermined axis and a bar holder arm having a predetermined curvature and extending from another end of the bar holder extended rod, wherein a bar gripper gripping a transverse coupling bar as a penetrator is provided at a tip of the bar holder arm, and the bar holder includes a release mechanism for releasing gripping of the bar gripper to install the rod-shaped transverse coupling bar in a predetermined position after the rod-shaped transverse coupling bar penetrates into and installed in a predetermined position.

11. A transverse installer for installing in a body a transverse coupler including a rod-shaped transverse coupling bar having a predetermined curvature in a longitudinal direction, the transverse coupler being an instrument used for transversely coupling at least two vertical couplers provided in order to vertically settle a spine by coupling screws inserted in vertebrae of the spine, the transverse installer comprising a positioning device for determining a position in which the transverse coupler is to be inserted and installed, and transverse insertion and installation tool percutaneously inserting and installing the transverse coupler, wherein the positioning device comprises:

at least two sizer bars and a mechanism that positions and attaches the at least two sizer bars in a predetermined position on each of the at least two vertical couplers before installation of the transverse coupler, and that releases the sizer bars from the vertical couplers after the installation of the transverse coupler;

the transverse insertion and installation tool comprises:

a penetrator that penetrates into a body;

a mechanism allowing the penetrator to move along an arc having a curvature substantially equal to the curvature when the penetrator penetrates into the body; and a fixing mechanism that fixes the arc in a position that is fixed relative to the positioning device during the movement; and the transverse installer enables the rod-shaped transverse coupling bar to percutaneously penetrate and be percutaneously installed along at least a portion of the arc;

wherein the transverse insertion and installation tool comprises:

a vertebra awl including at least one vertebra awl bar as an extended rod and a centering shaft rotatably supporting the vertebra awl bar on a predetermined axis, one end of the vertebra awl bar including a penetrator being a sharp-pointed vertebra awl tip configured to make a hole in the vertebra;

a soft-tissue awl including an awl extended rod rotatably supported at one end by a predetermined axis and radially extending from the predetermined axis and a penetrator having a predetermined curvature and extending from another end of the awl extended rod, wherein a sharp-pointed soft-tissue awl tip configured to make a hole in soft tissue is provided at a tip of the penetrator; and a bar holder including a bar holder extended rod rotatably supported at one end by a predetermined axis and radially extending from the predetermined axis and a bar holder arm having a predetermined curvature and extending from another end of the bar holder extended rod, wherein a bar gripper gripping a transverse coupling bar as a penetrator is provided at a tip of the bar holder arm, and the bar holder includes a release mechanism for releasing gripping of the bar gripper to install the rod-shaped transverse coupling bar in a predetermined position after the rod-shaped transverse coupling bar penetrates into and is installed in a predetermined position.

12. A surgical instrument used for attaching a transverse coupler, the surgical instrument comprising:

a sizer comprising:

two sizer bars;

a centering shaft rotatably supporting the two sizer bars on a predetermine axis; and a lock preventing rotation of the sizer bars with respect to the centering shaft;

wherein a rod gripping end is provided at one end of each of the sizer bars, so that each gripping end engages with a rod that couples screws inserted in vertebrae;

a vertebra awl comprising:

at least one vertebra awl bar equipped with a sharp-pointed vertebra awl tip configured to make a hole in the vertebra at one end of the vertebra awl bar; and wherein the centering shaft rotatably support the vertebra awl bar on the predetermined axis;

wherein the centering shaft is coaxial with the predetermined axis; and a hook holder comprising:

a hook holder extended rod rotationally supported at one end by the predetermined axis and radially extending from the predetermined axis; and a hook holder arm extending from another end of the hook holder extended rod;

wherein a hook gripper configured to grip at least one of the plurality of hooks is provided at a tip of the hook holder arm, and a bar holder comprising:

a bar holder extended rod rotatably supported at one end by the predetermined axis and radially extending from the predetermined axis; and a bar holder arm having a predetermined curvature and extending from another end of the bar holder extended rod;

wherein a bar gripper configured to grip a transverse bar is provided at a tip of the bar holder arm;

wherein the bar holder includes a release mechanism for releasing gripping of the bar gripper to install the transverse bar in a predetermined position after the transverse bar penetrates into a body and is installed in a predetermined position, wherein the transverse coupler comprises:

a plurality of hooks engaging with a rod that couples screws, wherein each of the screws is configured to be inserted in a vertebra; and a transverse bar having a predetermined curvature and provided between the plurality of hooks;

wherein the plurality of hooks includes a bar hole through which the transverse bar passes, a screw hole that communicates with the bar hole and a rod opening that engages with the rod;

wherein the bar hole communicates with the rod opening;

wherein the transverse coupler further includes a set screw configured to be screwed in the screw hole;

wherein when the set screw enters the screw hole, a tip of the set screw engages with and presses the transverse bar and the transverse bar pressed by the tip of the set screw presses the rod and pushes the rod against the rod opening; and wherein the bar hole of at least one of the plurality of hooks passes through the at least one of the plurality of hooks so that the transverse bar can be passed through the at least one of the plurality of hooks without being obstructed by the rod.

13. A surgical instrument used for attaching a transverse coupler, the surgical instrument comprising:

a sizer comprising:

two sizer bars;

a centering shaft rotatably supporting the two sizer bars on a predetermine axis; and a lock preventing rotation of the sizer bars with respect to the centering shaft;

wherein a rod gripping end is provided at one end of each of the sizer bars, so that each gripping end engages with a rod that couples screws inserted in vertebrae;

a vertebra awl comprising:
   at least one vertebra awl bar equipped with a sharp-pointed vertebra awl tip configured to make a hole in the vertebra at one end of the vertebra awl bar; and
   wherein the centering shaft rotatably support the vertebra awl bar on the predetermined axis;
   wherein the centering shaft is coaxial with the predetermined axis; and a hook holder comprising:
   a hook holder extended rod rotationally supported at one end by the predetermined axis and radially extending from the predetermined axis; and
   a hook holder arm extending from another end of the hook holder extended rod;
   wherein a hook gripper configured to grip at least one of the plurality of hooks is provided at a tip of the hook holder arm, and a bar holder comprising:
   a bar holder extended rod rotatably supported at one end by the predetermined axis and radially extending from the predetermined axis; and
   a bar holder arm having a predetermined curvature and extending from another end of the bar holder extended rod;
   wherein a bar gripper configured to grip a transverse bar is provided at a tip of the bar holder arm;
   wherein the bar holder includes a release mechanism for releasing gripping of the bar gripper to install the transverse bar in a predetermined position after the transverse bar penetrates into a body and is installed in a predetermined position;

wherein the transverse coupler comprises:
   a plurality of hooks engaging with a rod that couples screws, wherein each of the screws is configured to be inserted in a vertebra; and
   a transverse bar having a predetermined curvature and provided between the plurality of hooks;
   wherein the plurality of hooks includes a bar hole through which the transverse bar passes, a screw hole that communicates with the bar hole and a rod opening that engages with the rod;
   wherein the bar hole communicates with the rod opening;
   wherein the transverse coupler further includes a set screw configured to be screwed in the screw hole;
   wherein when the set screw enters the screw hole, a tip of the set screw engages with and presses the transverse bar and the transverse bar pressed by the tip of the set screw presses the rod and pushes the rod against the rod opening; and
   wherein the transverse bar is configured to pass through a spinous process of the vertebra.

\* \* \* \* \*